United States Patent
Lee et al.

(10) Patent No.: US 12,214,255 B2
(45) Date of Patent: Feb. 4, 2025

(54) GOLF BALL LOCATION ASCERTAINING METHOD AND A GOLF PLAY INFORMATION PROVIDING SYSTEM

(71) Applicant: SGM CO., LTD., Seongnam-si (KR)

(72) Inventors: Ui Bum Lee, Seongnam-si (KR); Kap Su Kim, Seoul (KR); Bok Sung Kwon, Namyangjyu-si (KR); Hyun Jin Choi, Namyangju-si (KR); Jae Hun Gwag, Seoul (KR)

(73) Assignee: SGM CO., LTD., Seongnam-si (KR)

( * ) Notice: Subject to any disclaimer, the term of this patent is extended or adjusted under 35 U.S.C. 154(b) by 345 days.

(21) Appl. No.: 17/873,147

(22) Filed: Jul. 26, 2022

(65) Prior Publication Data
US 2023/0032076 A1  Feb. 2, 2023

(30) Foreign Application Priority Data

Jul. 30, 2021 (KR) .......................... 10-2021-0100463
Oct. 5, 2021 (KR) .......................... 10-2021-0131566

(51) Int. Cl.
*A63B 69/36* (2006.01)
*A63B 24/00* (2006.01)

(52) U.S. Cl.
CPC ...... *A63B 24/0021* (2013.01); *A63B 24/0003* (2013.01); *A63B 2024/0031* (2013.01); *A63B 2024/0034* (2013.01); *A63B 2024/0053* (2013.01); *A63B 2220/836* (2013.01); *A63B 2225/50* (2013.01)

(58) Field of Classification Search
CPC ..... A63B 71/06; A63B 24/0021; A63B 57/00; A63B 69/36; A63B 2071/0691; A63B 2102/32; A63B 2220/10; A63B 2220/20; A63B 2024/0034; A63B 2024/0053; G01C 22/004
See application file for complete search history.

(56) References Cited

U.S. PATENT DOCUMENTS

2022/0284628 A1\* 9/2022 Tuxen ................ A63B 71/0616

FOREIGN PATENT DOCUMENTS

| KR | 10-2010-0047698 A | 5/2010 | |
|---|---|---|---|
| KR | 10-2014-0041083 A | 4/2014 | |
| KR | 10-1746662 B | 6/2017 | |
| KR | 10-2017-0093043 A | 8/2017 | |
| KR | 10-2018-0007361 A | 1/2018 | |
| KR | 10-2021-0079598 A | 6/2021 | |
| WO | WO-2013138381 A2 \* | 9/2013 | ............. A63B 53/00 |

\* cited by examiner

*Primary Examiner* — Lawrence S Galka
(74) *Attorney, Agent, or Firm* — You & IP, LLC

(57) ABSTRACT

The present invention relates to a golf ball location ascertaining method and a golf play information providing system. The golf ball location ascertaining method comprises a first step of ascertaining a motion location at which a predetermined motion is taken when a golfer located near a golf ball on a golf field takes the predetermined motion, and a second step of ascertaining the location of the golf ball on a golf course by using golf course data on the golf field and the motion location.

6 Claims, 21 Drawing Sheets

GOLF BALL LOCATION ASCERTAINING METHOD AND A GOLF PLAY INFORMATION PROVIDING SYSTEM

CROSS-REFERENCES TO RELATED APPLICATIONS

The present application is related to the Korean Patent Application No. 2021-0100463, filed Jul. 30, 2021 and Korean Patent Application No. 10-2021-0131566, filed Oct. 5, 2021, the entire disclosure of which is expressly incorporated by reference herein.

BACKGROUND OF THE INVENTION

1. Field of the Invention

The present invention relates to a golf ball location ascertaining method and a golf play information providing system.

2. Description of the Related Art

With a recent increase in the population of various sports, golf is also expanding its base as a popular sport. The population who enjoys golf has reached millions, and golf-related businesses have been greatly revitalized and thus the number of golf fields and the number of golf driving ranges continue to increase. Hundreds of domestic golf fields, including membership golf fields and public golf fields, are in operation, and the outlook for golf-related businesses is positive.

A golf course consists of 18 holes equipped with teeing ground, fairway, rough, green, hazard and bunker, and the 18 holes may consist of four par-5 holes, ten par-4 holes and four par-3 holes. The shortest par-3 hole has a course length (length from a tee shot location to a hole cup) of about 230 meters or less, and the longest par-5 hole has a course length of about 430 meters or more. Because the course length is considerable as described above, play information such as a distance between a golf ball and a hole cup is very important in golf. In order to ascertain the distance between the golf ball and the hole cup, golfers purchase a separate measuring device and use it on a golf field. However, the measuring device is expensive and thus it is economically burdensome to golfers. In addition, since there are areas on a golf course where distance measurement is not easy even by using the measuring device, there is a limit in obtaining necessary information with the measuring device.

BRIEF SUMMARY OF THE INVENTION

In order to solve the above-mentioned problems, the present invention provides a golf ball location ascertaining method that can accurately ascertain the location of a golf ball.

The present invention also provides a golf play information providing system that ascertains the location of a golf ball and informs a golfer of useful play information based on the ascertained location of the golf ball.

The other objects of the present invention will be clearly understood with reference to the following detailed description and the accompanying drawings.

In order to achieve the above-mentioned objects, a golf ball location ascertaining method according to an embodiment of the present invention comprises a first step of ascertaining a motion location at which a predetermined motion is taken when a golfer located near a golf ball on a golf field takes the predetermined motion and a second step of ascertaining the location of the golf ball on a golf course by using golf course data on the golf field and the motion location.

In the golf ball location ascertaining method, the predetermined motion comprises a swing motion in which the golfer hits the golf ball, and the swing motion is sensed by a wearable device worn by the golfer.

A golf play information providing system according to an embodiment of the present invention comprises a wearable device for detecting whether a golfer located near a golf ball on a golf field takes a predetermined motion while the wearable device is being worn by the golfer, a storage for storing golf course data on the golf field, and an information provider for ascertaining the location of the golf ball by using information about a location where the predetermined motion is taken and the golf course data stored in the storage and providing golf play information to the golfer based on the ascertained location of the golf ball.

The golf play information providing system further comprises a mobile device capable of communicating with the wearable device, and a location of the wearable device or a location of the mobile device is considered as the location where the predetermined motion is taken when the information provider ascertains the location of the golf ball.

The golf play information providing system further comprises a service device communicatively connected to the mobile device, and at least one of the information provider and the storage is provided in the mobile device or the service device.

In the golf play information providing system, the wearable device comprises a wristband that can be worn on the golfer's wrist.

A golf ball location ascertaining method according to another embodiment of the present invention comprises a step of checking whether a golfer takes a swing motion in a golf field, a step of ascertaining an motion location at which the swing motion is taken when it is determined that the swing motion is taken, and a step of ascertaining a location of the golf ball on a golf course by using golf course data on the golf field and the motion location.

In the golf ball location ascertaining method, there are a plurality of golfers, each of the plurality of golfers has a portable device capable of ascertaining his or her location, and whether the swing motion is made can be ascertained by checking a positional relationship between the plurality of golfers.

In the golf ball location ascertaining method, when any one of the plurality of golfers is positioned to be spaced apart from the other golfers positioned adjacent to each other for a predetermined time, a current location of the spaced apart golfer is considered as the motion location at which the swing motion is taken.

In the golf ball location ascertaining method, the step of ascertaining a location of the golf ball comprises dividing the golf course of the golf field into a plurality of areas and disposing cameras that have the same number of the plurality of divided areas and cover the divided areas respectively, generating photographed images for the divided areas using the cameras, extracting a photographed image including the golf ball among the photographed images, and ascertaining the location of the golf ball on the golf course by applying the extracted photographed image to golf course data on the area covered by the camera that is used to generate the extracted photographed image.

According to the present invention, the location of a golf ball on a golf field can be accurately ascertained, and useful play information based on the ascertained location of the golf ball can be provided to a golfer who is playing golf.

DETAILED DESCRIPTION OF THE INVENTION

Figure 1:
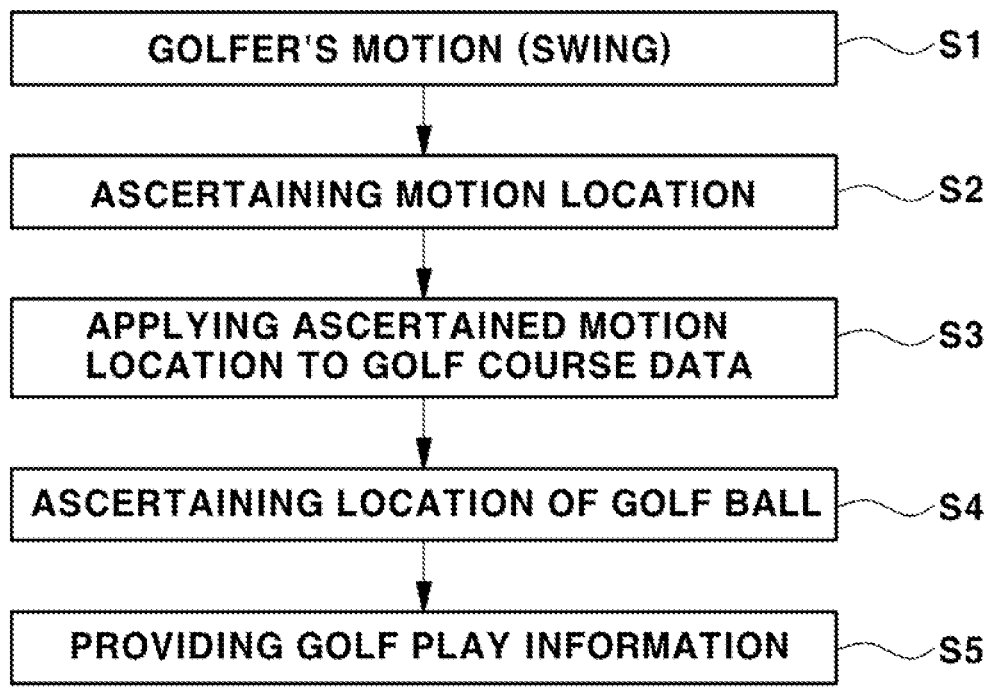
FIG. 1 is a flowchart showing an operation process of a golf play information providing method according to an embodiment of the present invention.

Hereinafter, a detailed description will be given of the present invention with reference to the following embodiments. The purposes, features, and advantages of the present invention will be easily understood through the following embodiments. The present invention is not limited to such embodiments but may be modified in other forms. The embodiments to be described below are nothing but the ones provided to bring the disclosure of the present invention to perfection and assist those skilled in the art to completely understand the present invention. Therefore, the following embodiments are not to be construed as limiting the present invention.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. It will be understood that when an element is referred to as being "on" another element, it can be directly on the other element or intervening elements may be present therebetween.

The size of the element or the relative sizes between elements in the drawings may be shown to be exaggerated for more clear understanding of the present invention. In addition, the shape of the elements shown in the drawings may be somewhat changed by variation of the manufacturing process or the like. Accordingly, the embodiments disclosed herein are not to be limited to the shapes shown in the drawings unless otherwise stated, and it is to be understood to include a certain amount of variation.

Figure 2:
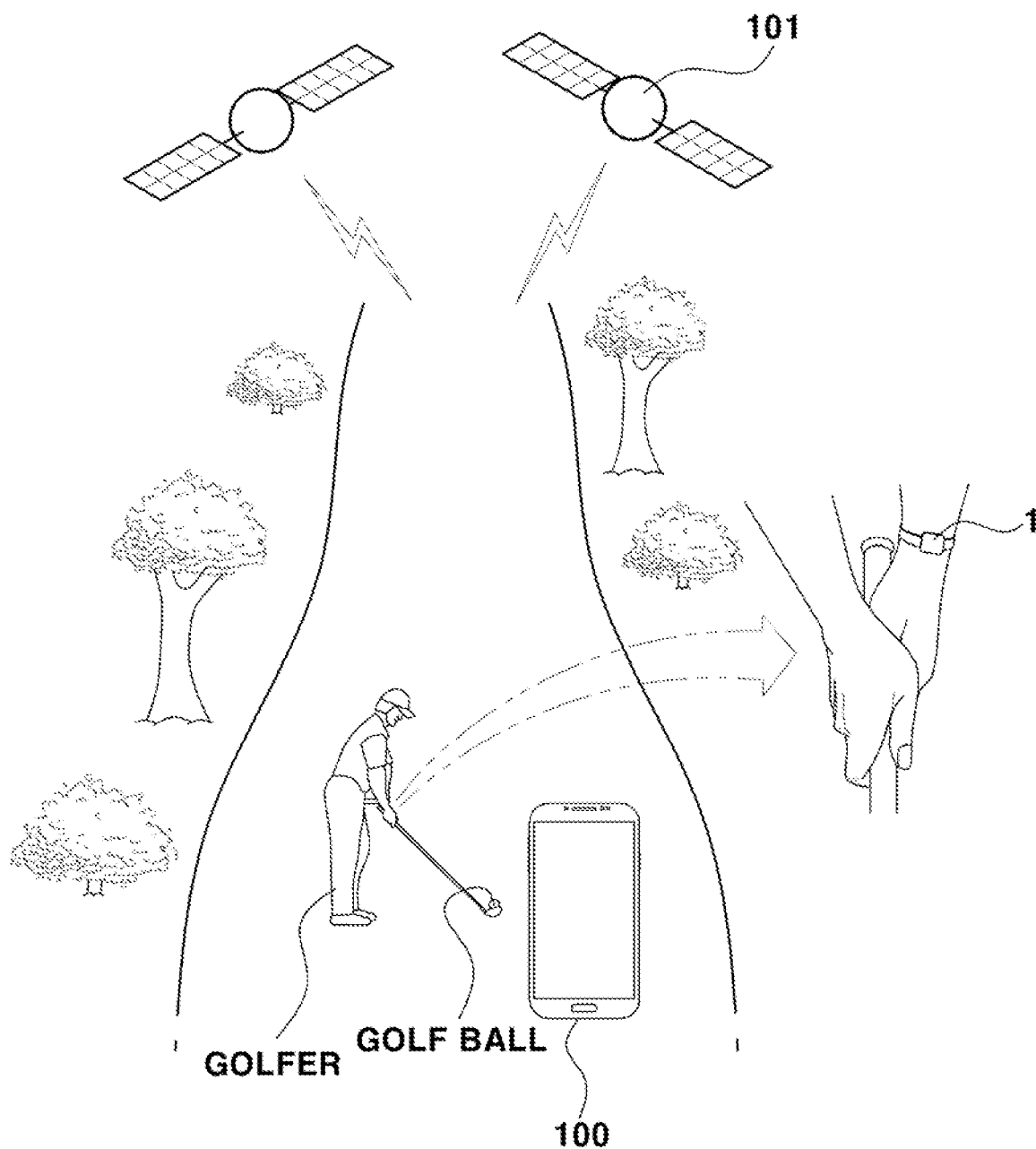
FIG. 2 is a view showing a schematic structure of a golf play information providing system according to an embodiment of the present invention.
Figure 3:
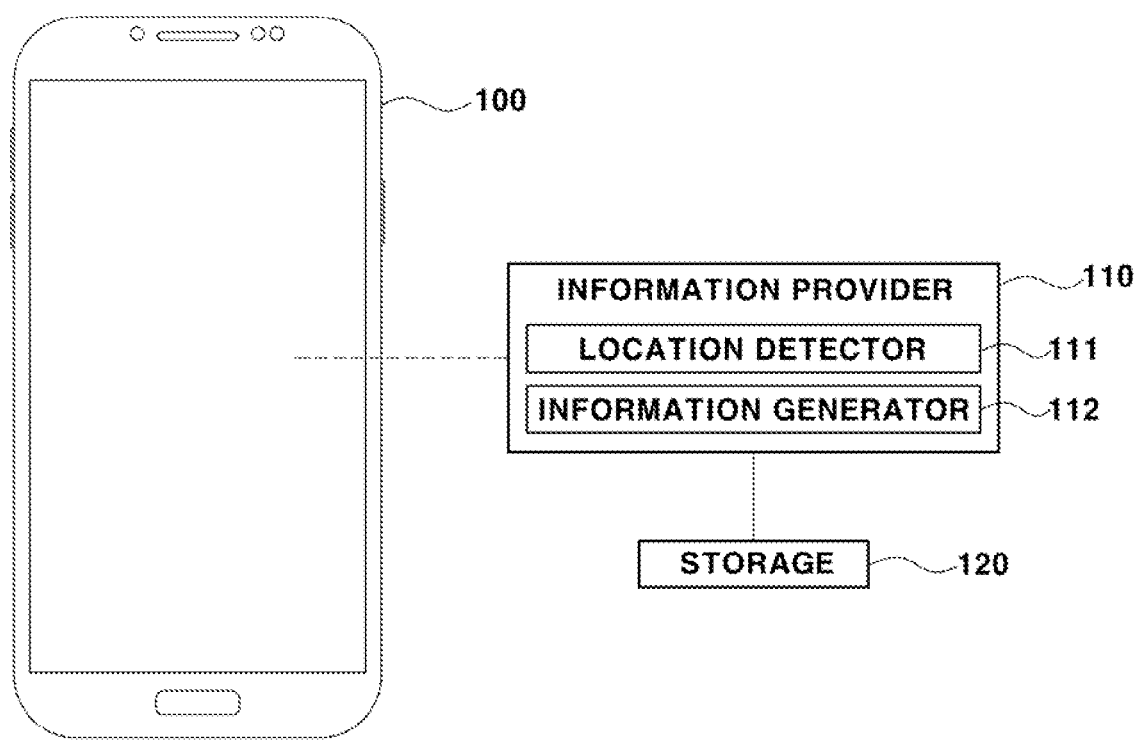
FIG. 3 is a view showing an example of a mobile device that can be used in the golf play information providing system of FIG. 2.

FIG. 1 is a flowchart showing an operation process of a golf play information providing method according to an embodiment of the present invention, FIG. 2 is a view showing a schematic structure of a golf play information providing system according to an embodiment of the present invention, FIG. 3 is a view showing an example of a mobile device that can be used in the golf play information providing system of FIG. 2, and FIGS. 4 through 7 are views showing individual processes of providing golf play information in the golf play information providing system of FIG. 2.

Referring to FIG. 1, the golf play information providing method according to the present embodiment includes a first step S1 in which a golfer makes a predetermined motion such as a swing motion, a second step S2 of ascertaining a location where the motion is made, a third step S3 of applying the ascertained motion location to golf course data, a fourth step S4 of ascertaining the location of a golf ball, and a fifth step S5 of generating golf play information based on the location of the golf ball and then providing the golf play information to a user. This golf play information providing method may be used in a golf play information providing system as shown in FIG. 2.

Referring to FIG. 2, the golf play information providing system includes a wearable device 1, a mobile device 100, and a GPS satellite 101. The wearable device 1 is worn on a golfer's body. As an example of the wearable device 1, a wristband type device that can be worn on the golfer's wrist is used. The wristband-type wearable device 1 may be equipped with a sensor capable of detecting a golfer's swing motion. For example, the wristband typed wearable device 1 may be equipped with a gyro sensor, an acceleration sensor, an impact detection sensor, and the like, and, when a golfer performs a swing motion while wearing the wearable device 1, the sensors detect the golfer's swing motion. The golfer's swing motion may be made not only when hitting a golf ball but also when making a practice swing without hitting the golf ball. Because the impact detection sensor can sense an impact generated when a golfer hits a golf ball, the impact detection sensor can distinguish a simple practice swing from a swing in which the golfer hits the golf ball and thus can detect a swing motion for hitting the golf ball. The object of sensing a swing for hitting the golf ball is to ascertain the location on which the golf ball is placed when the swing for hitting the golf ball is made. However, because the practice swing is generally made in the vicinity of the location on which the golf ball is placed before the golf ball is hit, there is no big difference between the location where the practice swing is made and the location where an actual swing for hitting the golf ball is made. Therefore, there is not a high need for distinguishing a practice swing from an actual swing for hitting a golf ball and the impact detection sensor is not essential. Alternatively, the wearable device 1 may include a separate input means such as a button, and a manual method in which a golfer wearing the wearable device 1 touches the button before hitting a golf ball and a location where the touch is made is considered as a location where a swing motion is made may also be applied. In this case, it is not necessary for a wristband to be provided with a detection sensor capable of detecting a swing motion.

A smartphone of the golfer may be used as the mobile device 100. Alternatively, a separate mobile device provided by a golf field being used by the golfer may be used as the mobile device 100. The separate mobile device may be used when golfers do not have their smartphones. Referring to FIG. 3, the mobile device 100 includes an information provider 110 and a storage 120. The information provider 110 provides golf play information, and the storage 120 stores data necessary to provide the golf play information. For example, the mobile device 100 can be furnished with the information provider 110 and the storage 120 by installing an app including a program performing an information provision role and related data on the mobile device 100. The golf play information can be generated based on an ascertained location of a golf ball, and the information provider 110 includes a location detector 111 ascertaining the location of the golf ball and an information generator 112 generating the golf play information.

The GPS satellite 101 is used to ascertain the location of the mobile device 100. When the mobile device 100 receives a signal from the GPS satellite 101, the location of the mobile device 100 may be ascertained. Here, a case of receiving a signal from the GPS satellite 101 in order to obtain location information of the mobile device 100 has been described. However, it is not essential to use a satellite signal to obtain the location information, and other methods of obtaining location information may be applied. A detailed process of providing golf play information according to the method of FIG. 1 in the system shown in FIGS. 2 and 3 is as follows.

Figure 4:
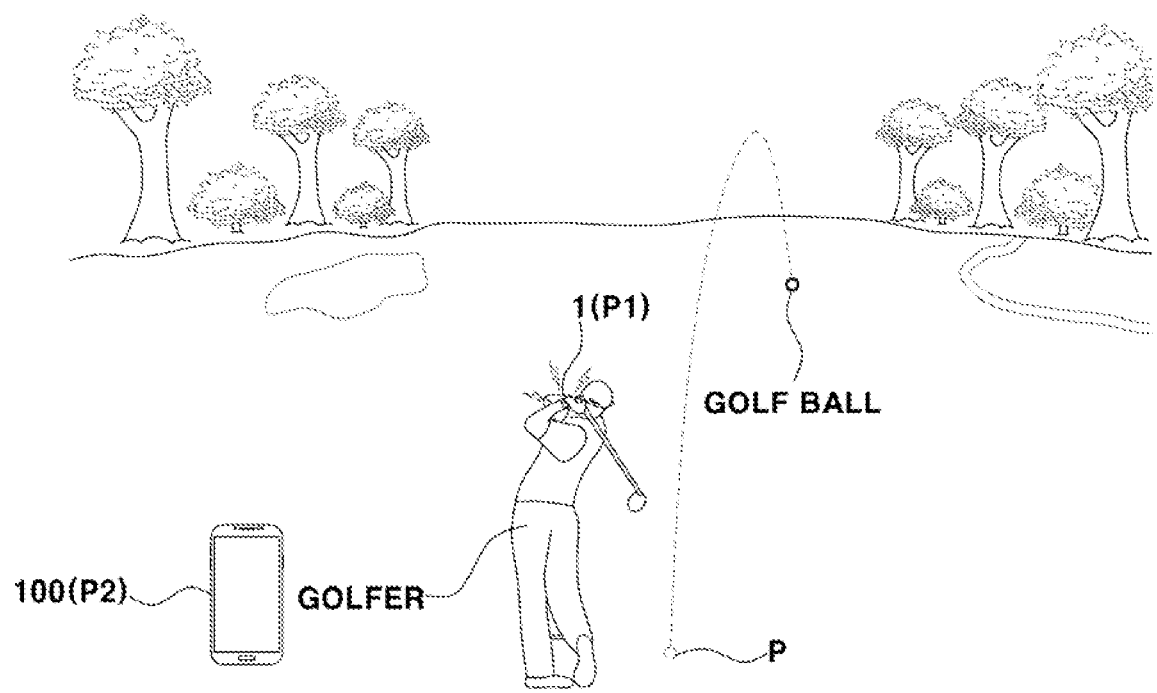
FIGS. 4 through 7 are views showing individual processes of providing golf play information in the golf play information providing system of FIG. 2.

Referring to FIG. 4, a golfer hits a golf ball while wearing the wearable device 1 on a golf field. As described above, the wearable device 1 is provided with a sensor capable of detecting a user's practice swing motion or a swing motion of hitting a golf ball, and, when the swing motion is sensed, a communication means separately included in the wearable device 1 transmits a signal to the mobile device 100. If the wearable device 1 is not provided with a sensor for detecting a swing motion, the golfer may manually inform the wearable device 1 that a swing is made at a current location, by using a separate input means before swinging. Even when the manual input method is used, the communication means may transmit a signal to the mobile device 100. When the mobile device 100 receives the transmitted signal, the mobile device 100 ascertains the location of the golf ball by using the GPS satellite 101 (See FIG. 2). When a location on which a golf ball is placed before being hit is referred to as a golf ball location P, a location of the wearable device 1 is referred to as a first location P1, and a location of the mobile device 100 is referred to as a second location P2, it is assumed in the present embodiment that the first location P1 or the second location P2 is the golf ball location P.

The first location P1, which is the location of the wearable device 1, is substantially the same as a location of a golfer wearing the wearable device 1. Because the golfer hits the golf ball in a state of being close to the golf ball, there may be no problem even when the location of the golfer (first location P1) is assumed to be the golf ball location P. If the mobile device 100 is a golfer's smartphone and the golfer has his or her smartphone while playing golf, the second location P2 becomes the golfer's location. In this case, since the golfer hits the golf ball in a state of being close to the golf ball, there is no problem even when the second location P2 is assumed to be the golf ball location P. If the mobile device 100 is spaced apart from the wearable device 1 to some extent, the second location P2 of the mobile device 100 can be first ascertained through a GPS satellite signal, the first location P1 can be then ascertained from the second location P2 by tracking the location of the wearable device 1 in the mobile device 100 through communication between the mobile device 100 and the wearable device 1, and the ascertained first location P1 can be considered as the golf ball location P.

Figure 5:
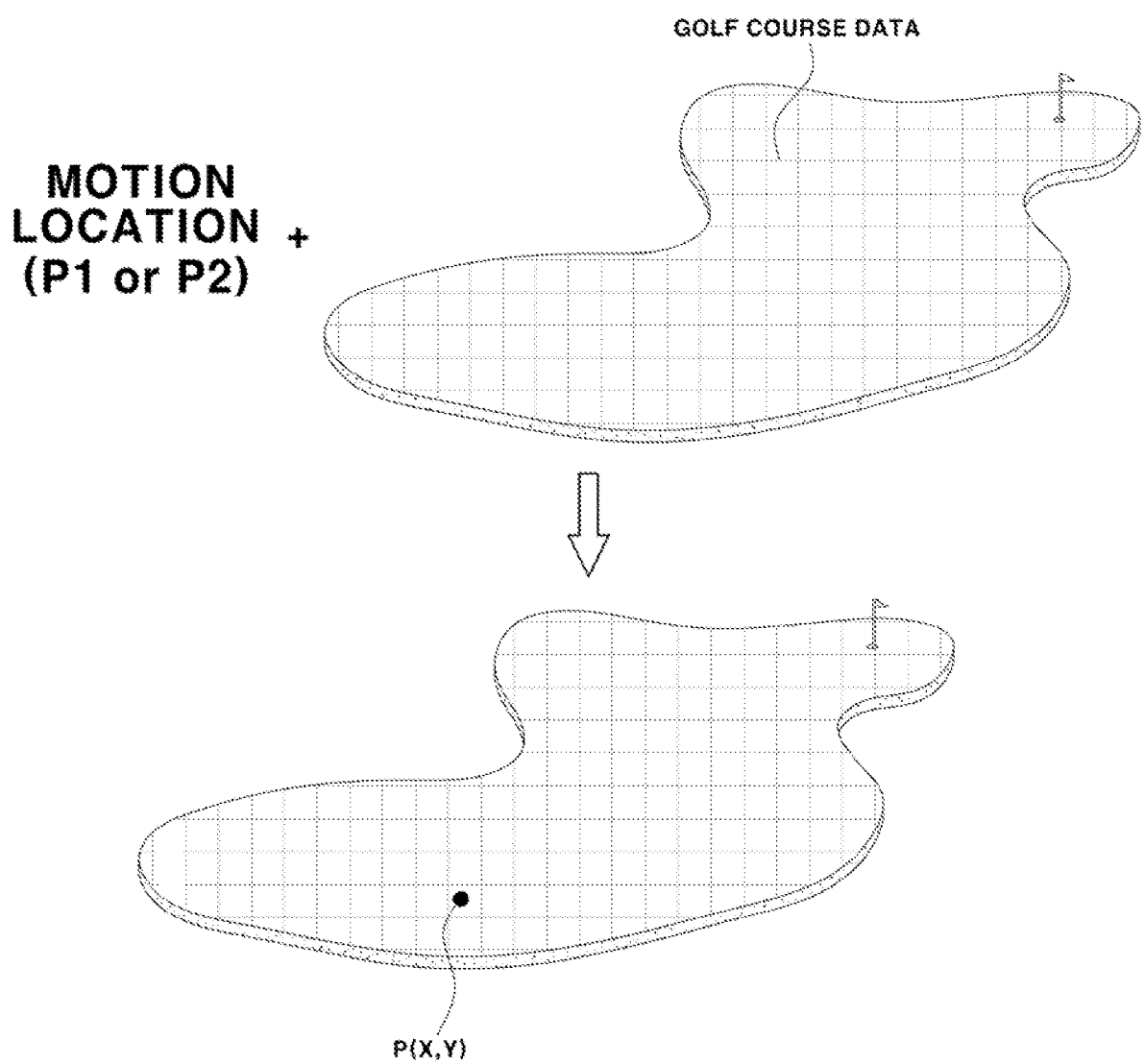

Referring to FIG. 5, information data on a golf course where a golfer is currently playing golf is stored in the storage 120, and the location detector 111 of the mobile device 100 extracts golf course data stored in the storage 120 and applies a motion location (first location P1 or second location P2) where the golfer's swing is made to the extracted golf course data. The golf course data may include golf course map data representing the map of the golf course where the golfer is currently playing golf, and coordinates may be set for each location on the map. When the motion location (first location P1 or second location P2) is coupled to the golf course map on which the coordinates have been set as described above, coordinates (X, Y) indicating the golf ball location P can be ascertained.

When the golf ball location P is identified by the location detector 111, the information generator 112 generates golf play information based on the identified golf ball location P and provides the generated golf play information to the golfer. There may be various pieces of golf play information.

Figure 6:
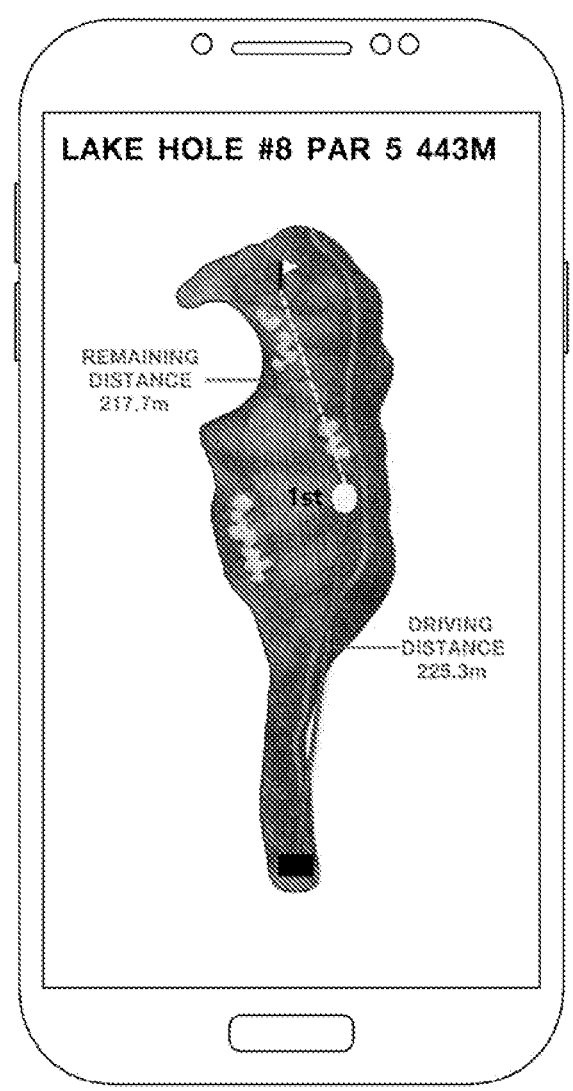
Figure 7:
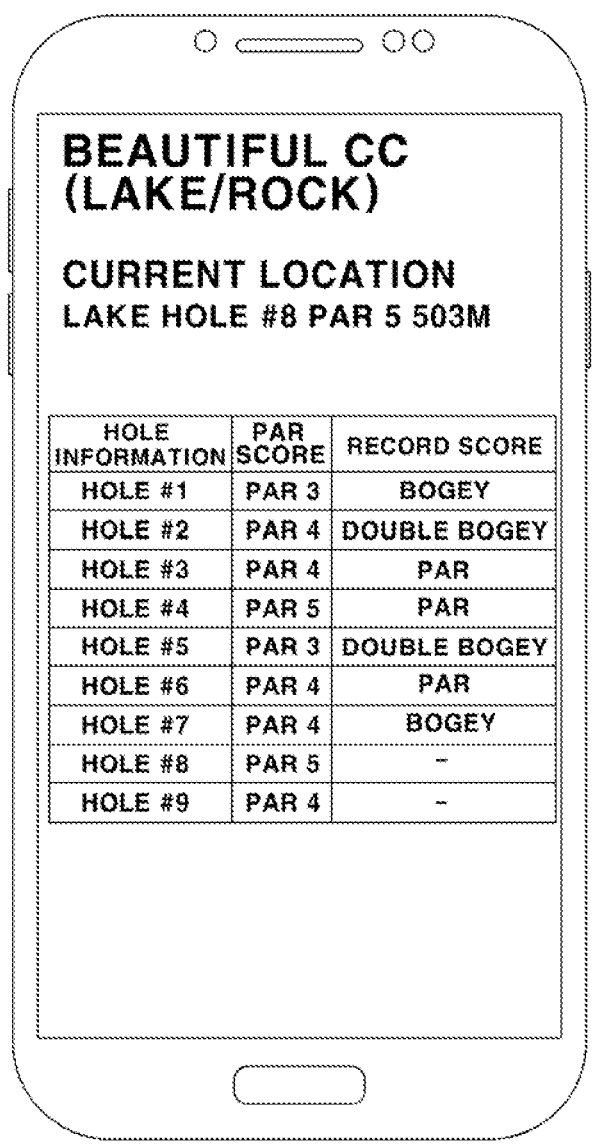

For example, when the current location of the golf ball is identified as coordinates, a distance and direction from the golf ball to a hole cup can be known. Accordingly, as shown in FIG. 6, the current location of the golf ball and the distance and direction from the golf ball to the hole cup can be provided as golf play information. In addition, if the location of the golf ball is ascertained whenever the user hits the golf ball, a hitting process (locations of the golf ball during every hitting) the user has gone through until reaching the current location of the golf ball can be known and be provided as golf play information to the golfer. Moreover, a final score can be ascertained by tracking the hitting process in each hole of the golf courses, and as shown in FIG. 7, a score record at each hole in the golf courses where golf is currently being played can be provided as golf play information to the golfer.

As above, after the location of the golf ball is ascertained, various pieces of play information such as the current location of the golf ball, the distance from the golf ball to the hole cup, the direction from the golf ball to the hole cup, and a hitting path of the golf ball and a score record in the golf course can be provided based on the ascertained position of the golf ball. When a golfer takes a specific motion and the location of a golf ball is ascertained by tracking the location of the specific motion, a significant effect can be produced by selecting a 'swing motion' as the specific motion and using a 'wristband' type wearable device to detect the swing motion. If a 'swing motion' is selected as a motion to start tracking the location of the golf ball, because the 'swing motion' is made in the vicinity of the location where the golf ball is placed, there is no problem even though the location of the swing motion is regarded as the location of the golf ball. In addition, if a motion other than a swing motion is selected as the motion for tracking the location of the golf ball, a golfer needs to take the motion separately during golf play. However, if a swing motion is selected as the motion for tracking the location of the golf ball as in the present embodiment, because the swing motion is an unconditionally necessary motion in golf play, a golfer does not need to take another separate motion in order to start tracking the location of the golf ball. Moreover, when a 'wristband' is used as a sensor for sensing the 'swing motion', the wristband can accurately catch a golfer's swing motion, because the arm of the golfer is moved whenever the golfer takes a swing motion and the arm movement is transmitted naturally to the wristband worn on the wrist. Furthermore, because the wristband is worn on the wrist, the wristband does not significantly interfere with the golfer's golf play. Like this, by selecting a 'swing motion' as the motion to start tracking the location of the golf ball and using a 'wristband' type as a device that senses the 'swing motion', two components, namely, the swing motion and the wristband, are combined with each other to thereby produce a significant effect.

Figure 8:
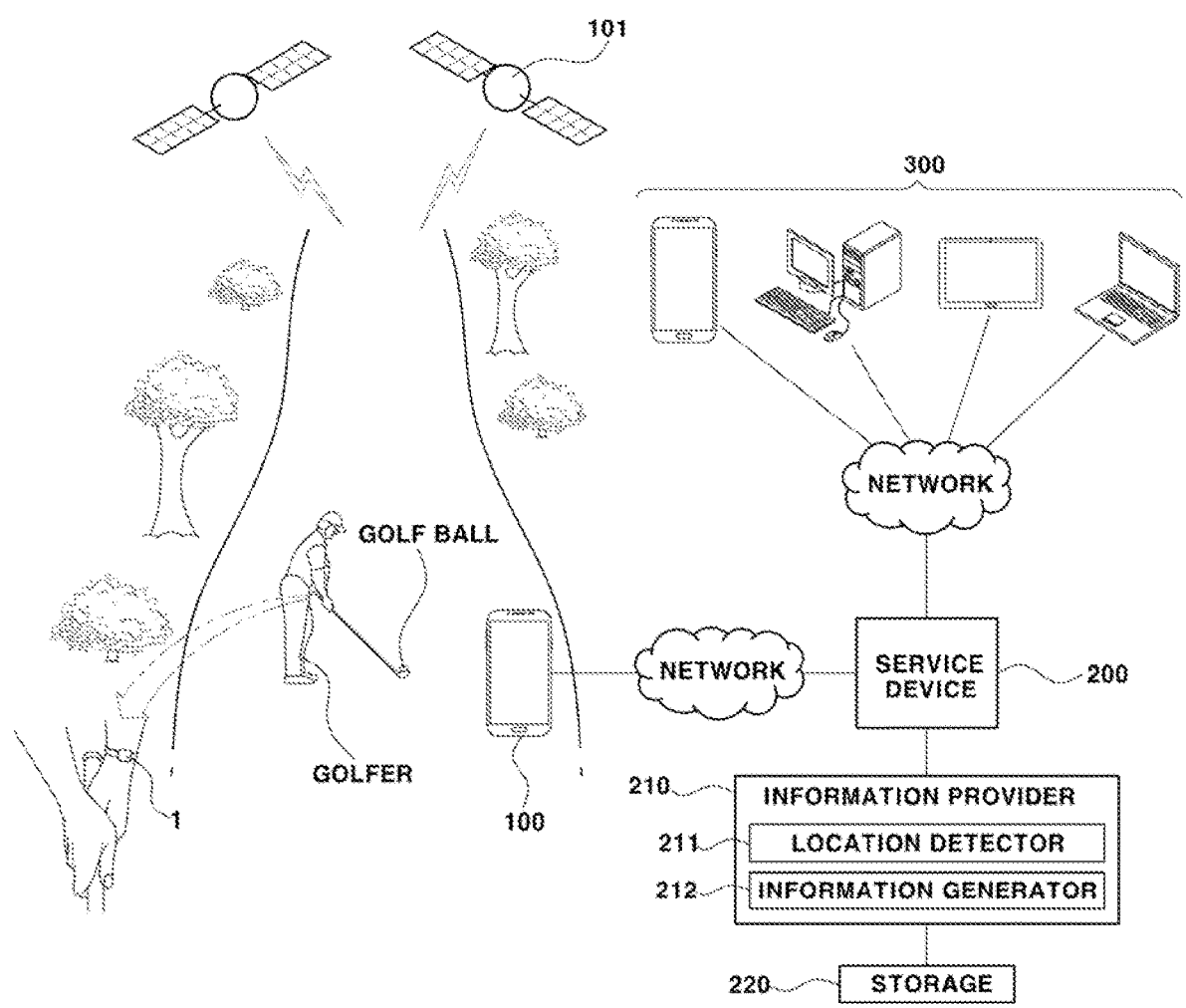
FIGS. 8 and 9 are views showing schematic structures of golf play information providing systems according to various other embodiments of the present invention.
Figure 9:
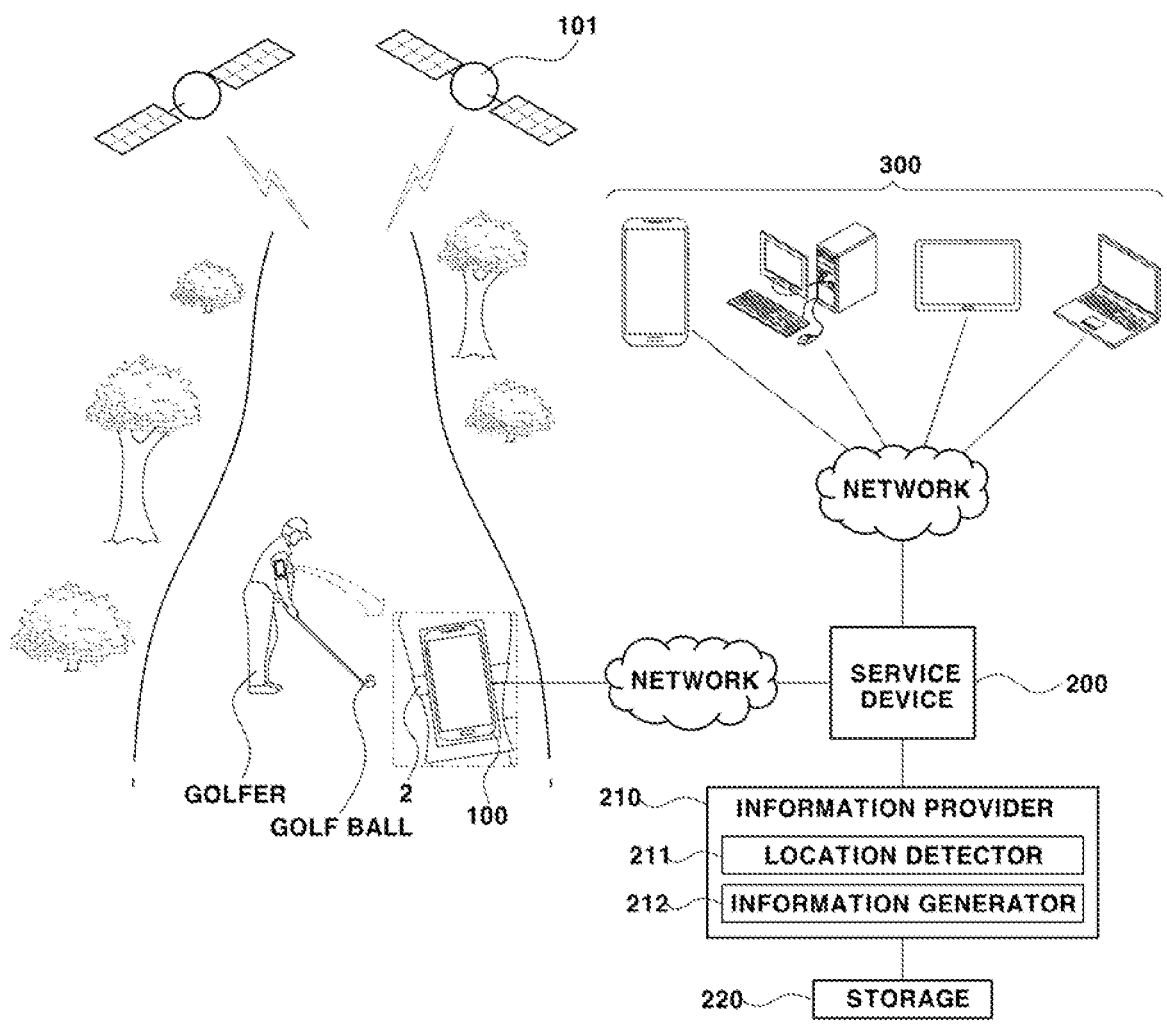
Figure 10:
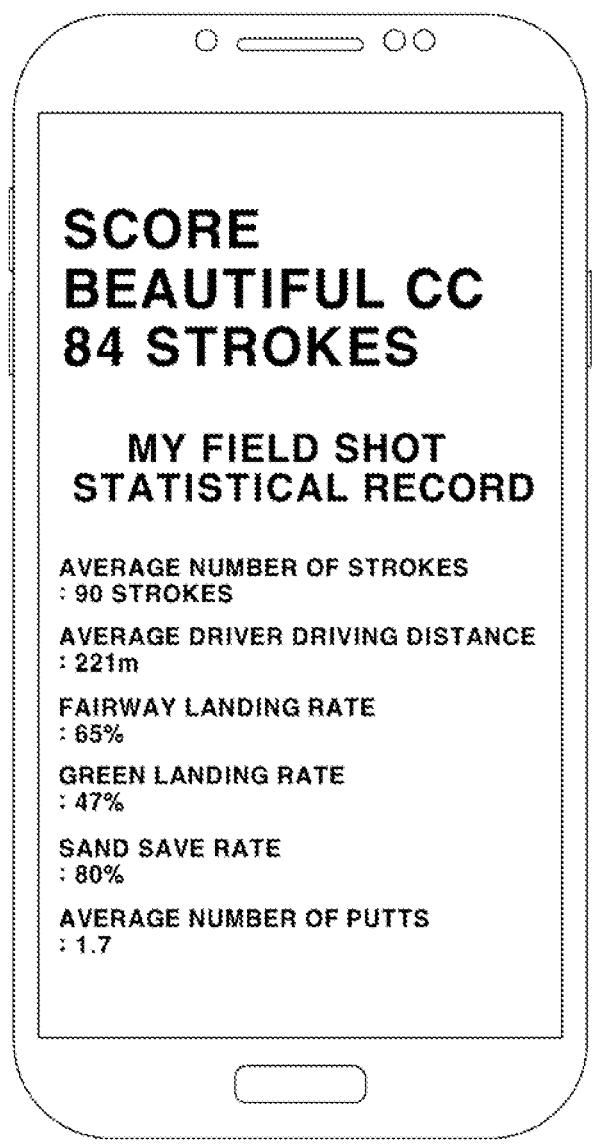
FIG. 10 is a view showing an example of golf play information provided by the golf play information providing systems of FIGS. 8 and 9.

FIGS. 8 and 9 are views showing schematic structures of golf play information providing systems according to various other embodiments of the present invention, FIG. 10 is a view showing an example of golf play information provided by the golf play information providing systems of FIGS. 8 and 9.

Referring to FIG. 8, the golf play information providing system according to the present embodiment includes a wearable device 1, a mobile device 100, a GPS satellite 101, a service device 200, and a terminal device 300. The wearable device 1 is worn on a golfer's body. As an example of the wearable device 1, a wristband type device that can be worn on the golfer's wrist is used. The wristband-type wearable device 1 may be equipped with a sensor capable of detecting a golfer's swing motion. Alternatively, the wearable device 1 may include a separate input means such as a button, and a manual method in which a golfer wearing the wearable device 1 touches the button before hitting a golf ball and a location where the touch is made is considered as a location where a swing motion is made may also be applied. As the mobile device 100, a golfer's own smart phone or the like may be used. The GPS satellite 101 may be used to ascertain the location of the mobile device 100. The service device 200 is connected to the mobile device 100 through a network, and various terminal devices 300 are connected to the service device 200 through a network. The terminal devices 300 can access the service device 200 through a wired and/or wireless network, and a smartphone, a desktop computer, a tablet computer, a laptop computer, etc. equipped with a web browser may be used as the terminal devices 300.

The service device 200 includes an information provider 210 and a storage 220. The information provider 210 provides golf play information, and includes a location detector 211 for ascertaining the location of a golf ball and an information generator 212 for generating golf play information. According to the present embodiment, the information provider 210 is included in the service device 200. However, the information provider 210 does not necessarily have to be included in the service device 200 but may be included in the mobile device 100. Alternatively, it is possible that only at least one of the location detector 211 and the information generator 212 of the information provider 210 is included in the mobile device 100. The storage 220 stores data necessary for providing golf play information. For example, the storage 220 stores golf course data of a golf field. Although not shown in FIG. 8, the service device 200 may be connected to a plurality of mobile devices 100 of a plurality of golfers through a network. In this case, the storage 220 may have a plurality of sections which are divided for the plurality of golfers and each of which stores the information of an individual golfer. The golfer's personal information and play information may be stored in each section for each golfer. The play information may include past play record of the golfer or personal record (average distance for each club, the average number of strokes, etc.) of the golfer obtainable from the past play record.

Like the above-described embodiment, in the golf play information providing system according to the present embodiment, when a golfer takes a swing motion the wearable device 1 detects the swing motion. When the swing motion is detected, the mobile device 100 ascertains a location (motion location) at which the swing motion has been made and transmits the ascertained location to the service device 200. In the information provider 210 of the service device 200, the position detector 211 applies the motion position to the golf course data to ascertain the location of the golf ball. In the information provider 210 of the service device 200, the information generator 212 generates golf play information based on the ascertained golf ball's location. The generated golf play information is transmitted from the service device 200 to the mobile device 100, and the mobile device 100 displays the received golf play information to provide it to the golfer. The golf play information may be provided not only to a golfer currently playing golf through the mobile device 100, but also to various terminal devices 300, and the golfer or other users can receive the golf play information at any desired time by using the terminal devices 300.

In the embodiment shown in FIG. 8, the wearable device 1 is not essential and may be omitted. For example, as shown in FIG. 9, instead of using the wearable device 1, a golfer may wear an armband 2 on his or her arm and the mobile device 100 may be mounted on the armband 2. A smartphone of the golfer may be used as the mobile device 100. When the smartphone is equipped with a sensor capable of sensing a golfer's swing motion, the smartphone mounted on the armband 2 may perform both the roles of the wearable device 1 and the mobile device 100 according to the embodiment of FIG. 8. In other words, the golfer's swing motion may be sensed through the smartphone, and the location of the golf ball at a location where the swing motion has been made may be ascertained through a location tracking function of the smartphone.

When the location of the golf ball is ascertained, various pieces of golf play information may be provided based on the ascertained location. The various pieces of golf play information may include the current location of the golf ball, the distance from the golf ball to the hole cup, the direction from the golf ball to the hole cup, and a hitting path of the golf ball and a score record in the golf course where golf is being played. In addition, because the storage 220 stores the golfer's past play record or the golfer's personal record calculated from the golfer's past play record, golf play information including the play record may be provided. For example, as shown in FIG. 10, personal record information such as the average number of strokes of the golfer, an average driver driving distance, a fairway landing rate, a green landing rate, a sand save rate, and the average number of putts may be provided as the golf play information.

Figure 11:
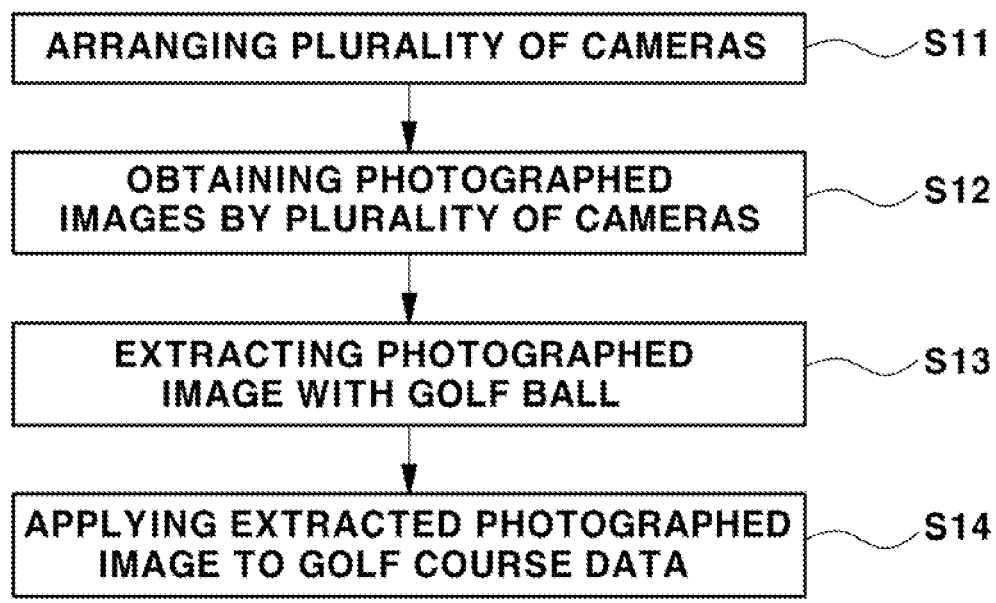
FIG. 11 is a flowchart showing an operation process of a golf ball location ascertaining method according to an embodiment of the present invention.
Figure 12:
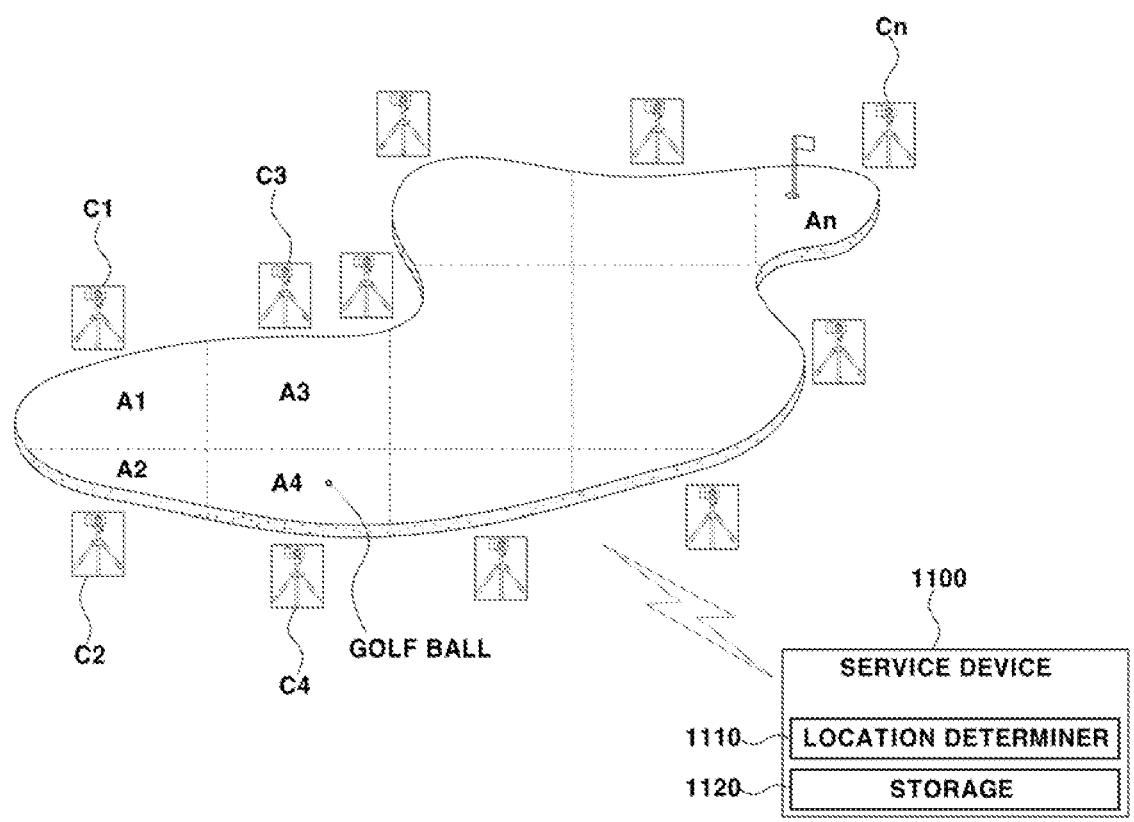
FIG. 12 is a view showing a schematic structure of a golf ball location ascertaining system according to an embodiment of the present invention.
Figure 13:
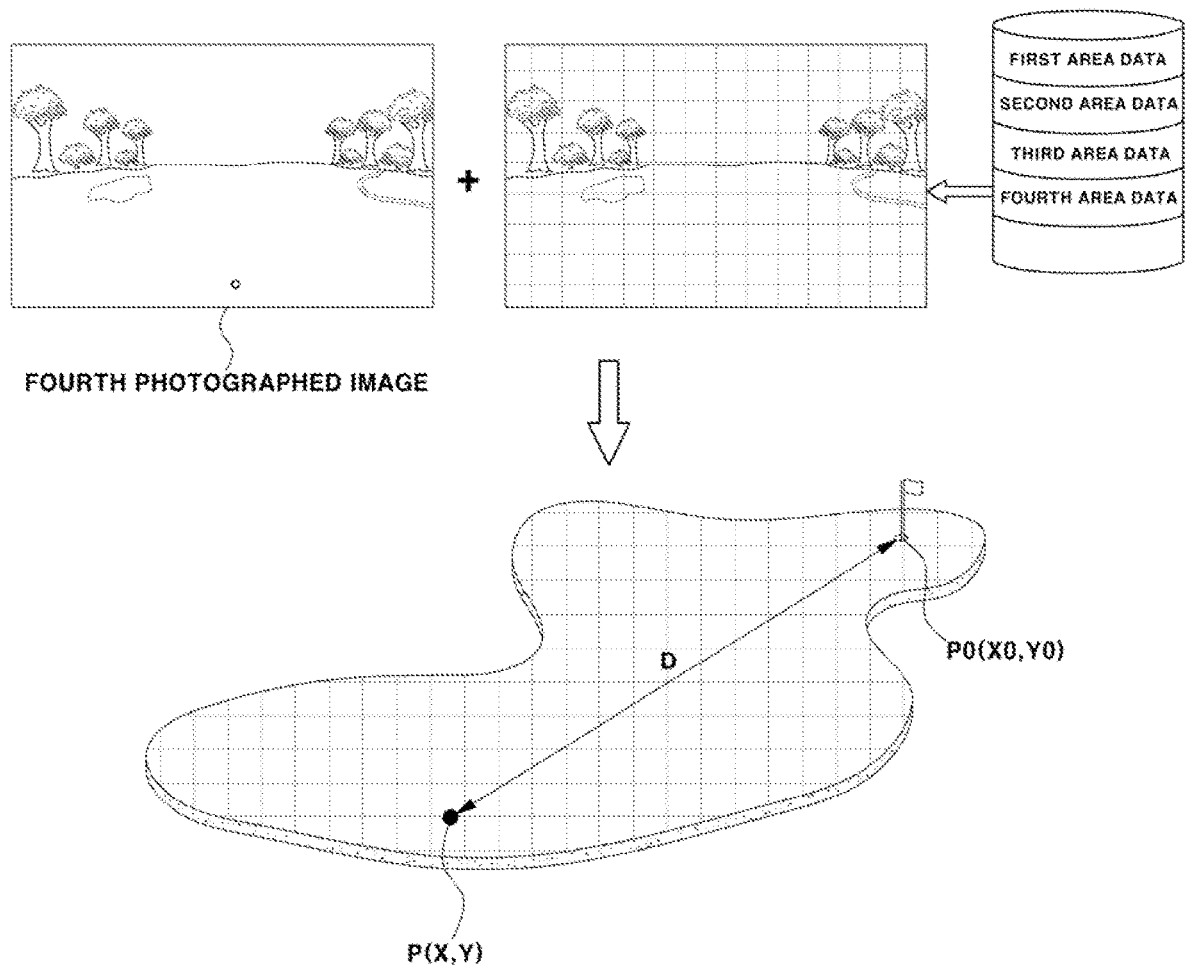
FIG. 13 is a view for explaining an operating principle when the golf ball location ascertaining method of FIG. 11 is applied to the golf ball location ascertaining system of FIG. 12.

FIG. 11 is a flowchart showing an operation process of a golf ball location ascertaining method according to an embodiment of the present invention, FIG. 12 is a view showing a schematic structure of a golf ball location ascertaining system according to an embodiment of the present invention and FIG. 13 is a view for explaining an operating principle when the golf ball location ascertaining method of FIG. 11 is applied to the golf ball location ascertaining system of FIG. 12.

Referring to FIG. 11, the golf ball location ascertaining method according to the present embodiment includes a first step S11 through a fourth step S14. In the first step S11, the golf course of a golf field is divided into a plurality of areas, and cameras covering the divided plurality of areas are disposed in the plurality of areas. In the second step S12, each of the plurality of cameras photographs an area covered by each of the plurality of cameras to generate a photographed image. In the third step S13, a photographed image with a golf ball is extracted from among a plurality of photographed images obtained by the plurality of cameras. In the fourth step S14, the location of the golf ball is ascertained by applying the extracted photographed image to golf course data on an area covered by the camera obtaining the extracted photographed image. This golf gall location ascertaining method may be used in a golf gall location ascertaining system as shown in FIG. 12.

Referring to FIG. 12, the golf ball location ascertaining system includes a plurality of cameras C1, C2, . . . , and Cn and a service device 1100. The plurality of cameras C1, C2, . . . , and Cn are disposed throughout the golf field, and may cover respective areas allocated thereto. For example, when the golf course of the golf field is divided into N zones and the N zones are a first area A1, a second area A2, . . . , and an N-th area An (where the division areas may overlap each other or not overlap each other), N cameras C1, C2, . . . , and Cn are arranged. Assuming that the N cameras C1, C2, . . . , and Cn are a first camera C1, a second camera C2, . . . , and an N-th camera Cn, respectively, the first camera C1 covers the first area A1, the second camera C2 covers the second area A2, . . . , and the N-th camera Cn covers the Nth area An. Herein, the meaning that a K-th camera (where K is a natural number between 1 and N) covers a K-th area is that an area photographed by the K-th camera may cover the entire K-th area. The service device 1100 serves to ascertain the location of a golf ball and transmit the ascertained location of the golf ball to a golfer, and includes a location determiner 1110 for ascertaining the location of the golf ball and a storage 1120 for storing golf course data, etc. necessary for ascertaining the location of the golf ball. Although not shown in the drawings, both the plurality of cameras C1, C2, . . . , and Cn and the service device 1100 are provided with wireless communication means and may communicate with each other by using the wireless communication means.

When the golf ball location ascertaining method of FIG. 11 is applied to the golf ball location ascertaining system of FIG. 12, the first step S11 in the golf ball location ascertaining method is performed by the golf ball location ascertaining system itself, because, in the golf ball location ascertaining system, the golf course is divided into N areas and the cameras C1, C2, . . . , and Cn are arranged in the N areas, respectively. In the second step S12, the cameras C1, C2, . . . , and Cn generates photographed images by photographing the areas respectively covered by the cameras C1, C2, . . . , and Cn. A photographed image (first photographed image) for the first area A1 is obtained by the first camera C1, a photographed image (second photographed image) for the second area A2 is obtained by the second camera C2, . . . , and a photographed image (N-th photographed image) for the N-th area An is obtained by the N-th camera Cn. In the third step S13, the obtained first through N-th photographed images are transmitted to the service device 1100, and the position determiner 1110 of the service device 1100 analyzes the first through N-th photographed images to extract the photographed image with the golf ball from among the first through N-th photographed images. Referring to FIG. 13, if it is assumed that the golf ball is identified in a fourth photographed image (image obtained by a fourth camera C4 photographing a fourth area A4), the location determiner 1110 applies the fourth photographed image to the golf course data stored in the storage 1120, in the fourth step S4. The golf course data may include first area data, second area data, . . . , and N-th area data corresponding to the first through N-th areas A1, . . . , and An, respectively. By using K-th area data (where K is a natural number between 1 and N), a plurality of horizontal lines/vertical lines can be applied to a K-th photographed image so that coordinates at a specific location on the K-th photographed image may be specified. Accordingly, when the fourth photographed image is applied to the fourth area data, the coordinates at the location of the golf ball on the fourth photographed image may be known. As a result, as shown in FIG. 13, coordinates (X, Y) at a current golf ball location P on a golf course can be known.

Location information P (X, Y) of the ascertained golf ball location may be used in various ways. First, a distance D between the golf ball and the hole cup can be ascertained using the location information P (X, Y) of the golf ball and location information P0(X0, Y0) of the hole cup on the golf course, and can be provided as golf play information to a golfer. Although not shown in the drawings, the golfer may possess a mobile device such as a smartphone. In this case, the mobile device can communicate with the service device 1100 to receive golf play information such as the distance D between the golf ball and the hole cup from the service device 1100 and show the received golf play information on the display to provide it to a user. Second, when the location information P (X, Y) of the golf ball indicates the location where the golfer's golf ball was hit and all the locations where the golf ball was hit in a specific golf course are collected, a hitting path (locations of the golf ball during every hitting) the golfer has gone through in the specific golf course can be ascertained and thus the user's score on the corresponding golf course can also be ascertained.

Figure 14:
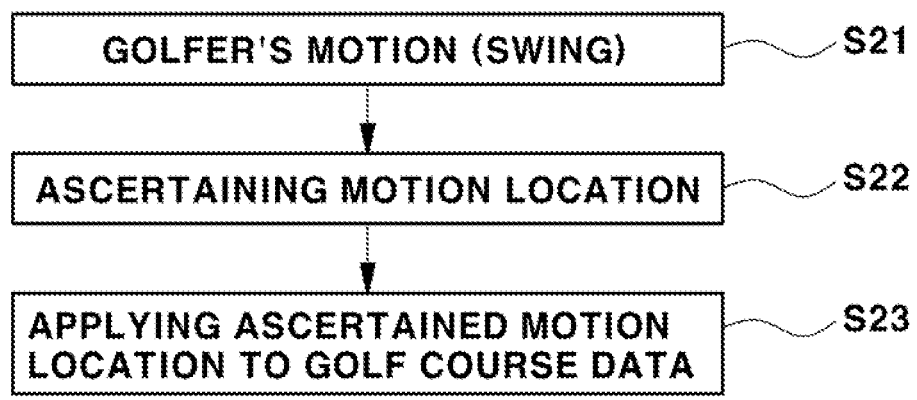
FIG. 14 is a flowchart showing an operation process of a golf ball location ascertaining method according to another embodiment of the present invention.
Figure 15:
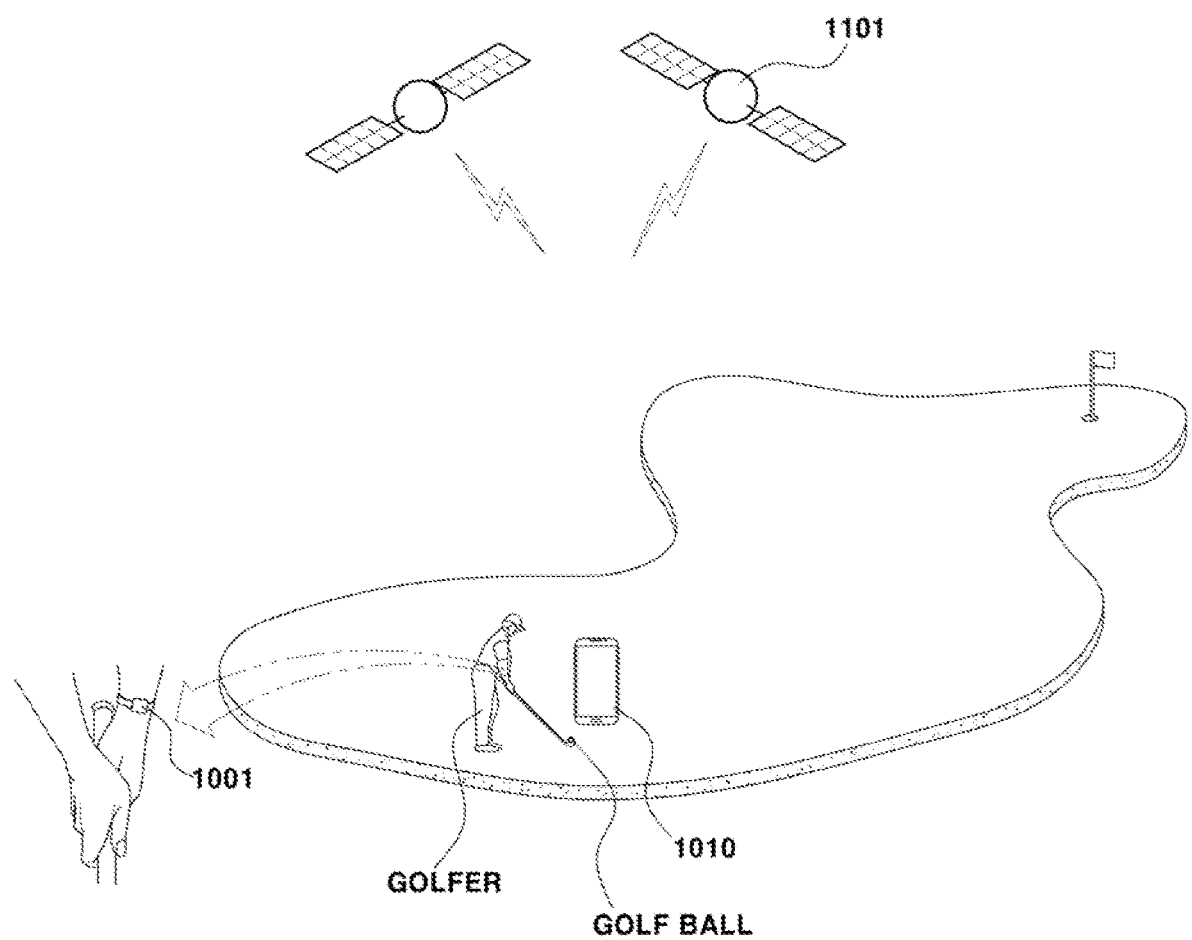
FIG. 15 is a view showing a schematic structure of a golf ball location ascertaining system according to another embodiment of the present invention.
Figure 16:
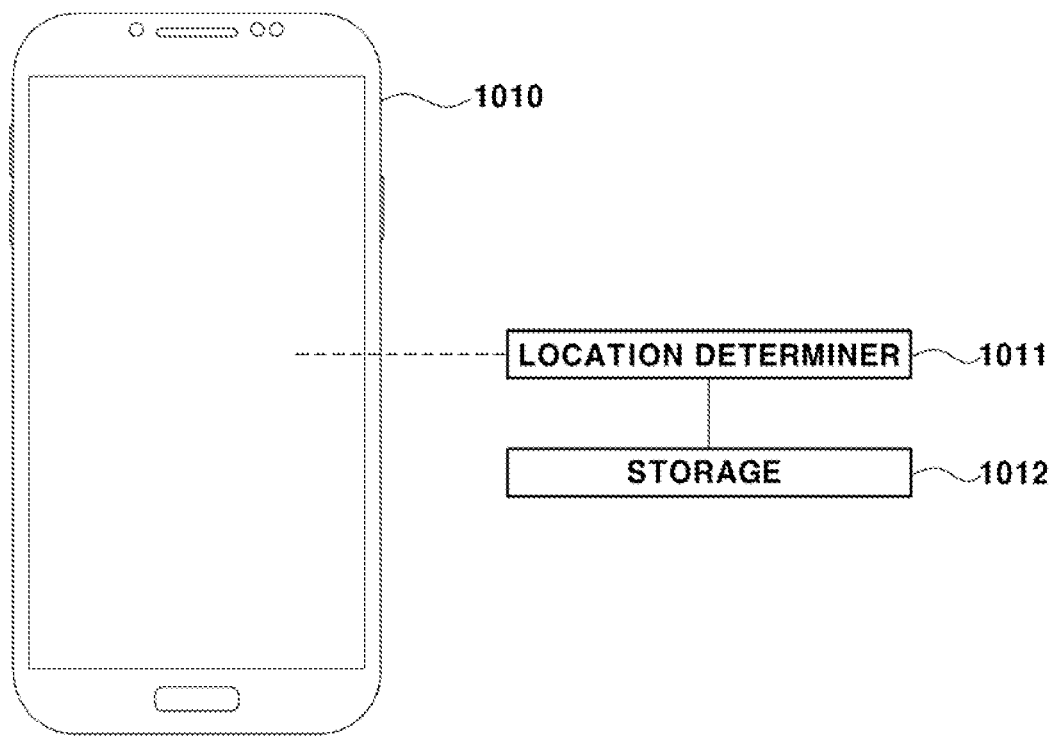
FIG. 16 is a view showing an example of a mobile device that can be used in the golf ball location ascertaining system of FIG. 15.
Figure 17:
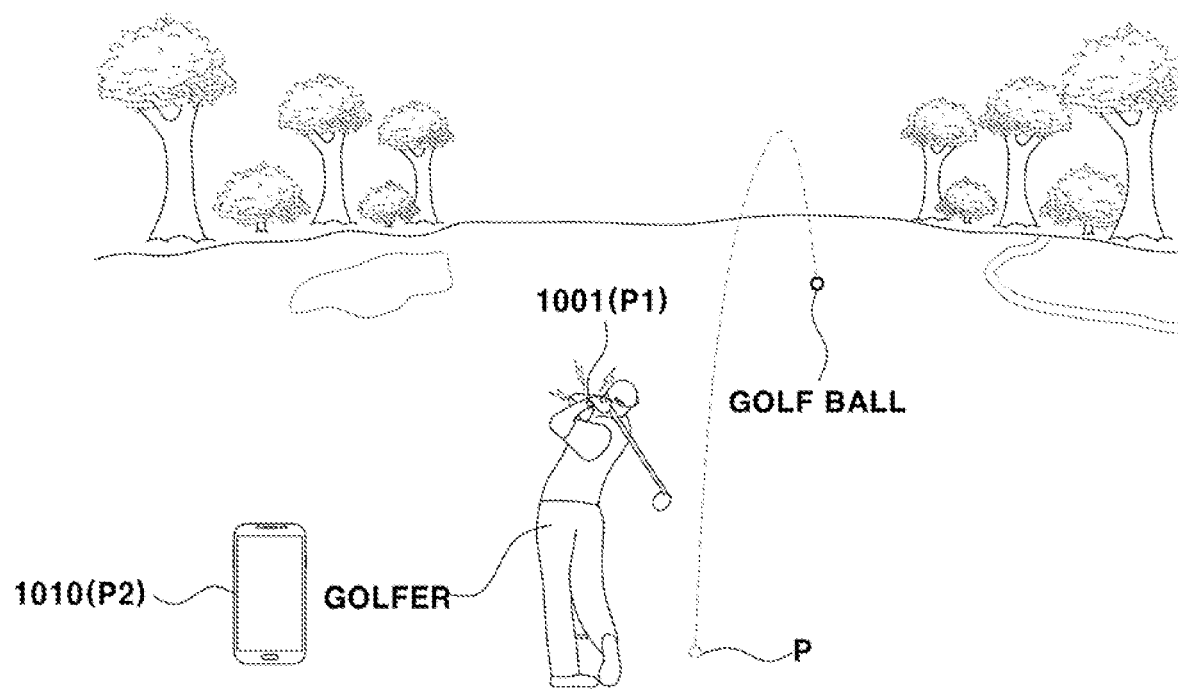
FIGS. 17 and 18 are views for explaining an operating principle when the golf ball location ascertaining method of FIG. 14 is applied to the golf ball location ascertaining system of FIG. 15.
Figure 18:
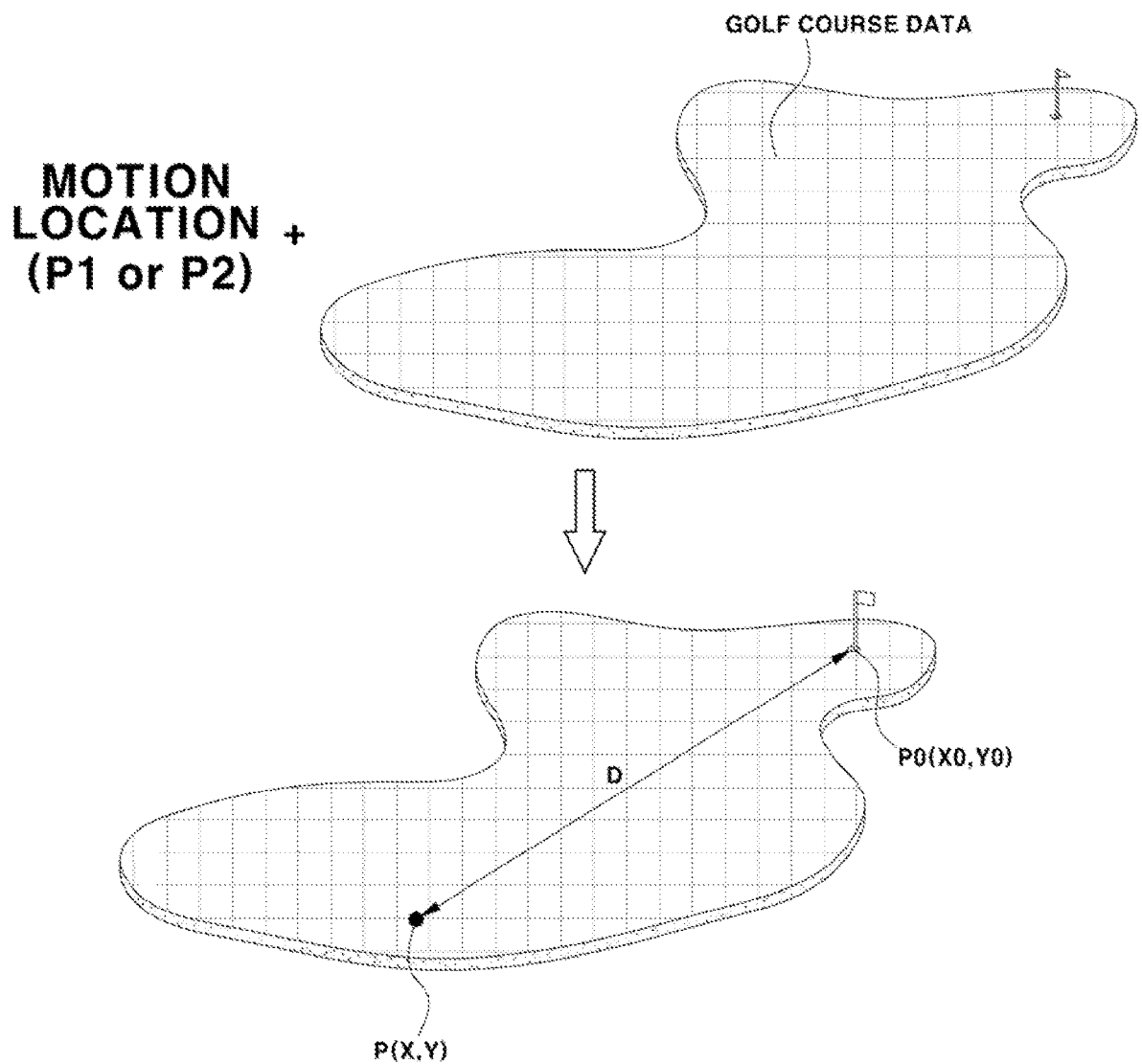

FIG. 14 is a flowchart showing an operation process of a golf ball location ascertaining method according to another embodiment of the present invention, FIG. 15 is a view showing a schematic structure of a golf ball location ascertaining system according to another embodiment of the present invention, FIG. 16 is a view showing an example of a mobile device that can be used in the golf ball location ascertaining system of FIG. 15, and FIGS. 17 and 18 are views for explaining an operating principle when the golf ball location ascertaining method of FIG. 14 is applied to the golf ball location ascertaining system of FIG. 15.

Referring to FIG. 14, the golf ball location ascertaining method according to the present embodiment includes first through third steps S21 through S23. In the first step S21, it is checked whether a golfer takes a swing motion on a golf field. In the second step S22, a motion location at which the swing motion is made is ascertained. In the third step S23, the location of the golf ball on a golf course is ascertained by applying the ascertained motion location to golf course data on the golf field. This golf gall location ascertaining method may be used in a golf gall location ascertaining system as shown in FIG. 15.

Referring to FIG. 15, the golf gall location ascertaining system includes a wearable device 1001 and a mobile device 1010 that are portable. The wearable device 1001 is worn on a golfer's body. As an example of the wearable device 1001, a wristband type device that can be worn on the golfer's wrist is used. The wristband-type wearable device 1001 may be equipped with a sensor capable of detecting a golfer's swing motion. For example, the wristband typed wearable device 1001 may be equipped with a gyro sensor, an acceleration sensor, an impact detection sensor, and the like, and, when a golfer performs a swing motion while wearing the wearable device 1001, the sensor may detect the golfer's swing motion. The golfer's swing motion may be made not only when hitting a golf ball but also when making a practice swing without hitting the golf ball. Because the impact detection sensor can sense an impact generated when a golfer hits a golf ball, the impact detection sensor can distinguish a simple practice swing from a swing in which the golfer hits the golf ball and thus can detect a swing motion for hitting the golf ball. The object of sensing a swing for hitting the golf ball is to ascertain the location on which the golf ball is placed when the swing for hitting the golf ball is made. However, because the practice swing is generally made in the vicinity of the location on which the golf ball is placed before the golf ball is hit, there is no big difference between the location where the practice swing is made and the location where an actual swing for hitting the golf ball is made. Therefore, there is not a high need for distinguishing a practice swing from an actual swing for hitting a golf ball and the impact detection sensor is not essential.

When the location on which the golf ball is placed is ascertained from the location where the practice swing is made, play information generated based on the ascertained location may be provided to the golfer before the golf ball is actually hit by the golfer. When the location on which the golf ball is placed is ascertained from the location where a swing actually hitting the golf ball is made, the ascertained location may be used to generate the golfer's play record. As an example of the golfer's play record, there is a play record regarding a hitting path representing a path of locations of the golf ball during every hitting from a tee box to a hole cup.

The wearable device 1001 may include a separate input means such as a button, and a manual method in which a golfer wearing the wearable device 1001 touches the button before hitting a golf ball and a location where the touch is made is considered as a location where a swing motion is made may also be applied. In this case, it is not necessary for a wristband to be provided with a detection sensor capable of detecting a swing motion.

A smartphone of the golfer may be used as the mobile device 1010. Alternatively, a separate mobile device provided by a golf field being used by the golfer may be used as the mobile device 1010. The separate mobile device may be used when golfers do not have their smartphones. Referring to FIG. 16, the mobile device 1010 includes a location determiner 1011 and a storage 1012. The location determiner 1011 ascertains the location of the golf ball and provides golf play information such as a distance between the golf ball and the hole cup, and the storage 1012 stores data necessary to provide the golf play information. For example, the mobile device 1010 can be furnished with the location determiner 1011 and the storage 1012 by installing an app including a program ascertaining the location of the golf ball and performing an information provision role and related data on the mobile device 1010.

When a smartphone is used as the mobile device 1010, the mobile device 1010 may receive a signal from the GPS satellite 1101, and thus the location of the mobile device 1010 may be ascertained. Here, a case of receiving a signal from the GPS satellite 1101 in order to obtain location information of the mobile device 1010 has been described. However, it is not essential to use a satellite signal to obtain the location information, and other methods of obtaining location information may be applied.

When the golf ball location ascertaining method of FIG. 14 is applied to the golf ball location ascertaining system of FIG. 15, the golfer hits the golf ball while wearing the wearable device 1001, in the first step S21 of the golf ball location ascertaining method, as shown in FIG. 17. The wearable device 1001 is provided with a sensor capable of detecting a user's practice swing motion or a swing motion of hitting a golf ball, and, when the swing motion is sensed, a communication means separately included in the wearable device 1001 transmits a signal to the mobile device 1010. If the wearable device 1001 is not provided with a sensor for detecting a swing motion, the golfer may manually inform the wearable device 1001 that a swing is made at a current location, by using a separate input means before swinging. Even when the manual input method is used, the communication means may transmit a signal to the mobile device 1010. In the second step S22, when the mobile device 1010 receives the transmitted signal, the mobile device 1010 ascertains the location of the golf ball by using the GPS satellite 1101 (See FIG. 15). When a location on which a golf ball is placed before being hit is referred to as a golf ball location P, a location of the wearable device 1001 is referred to as a first location P1, and a location of the mobile device 1010 is referred to as a second location P2, it is assumed in the present embodiment that the first location P1 or the second location P2 is the golf ball location P.

The first location P1, which is the location of the wearable device 1001, is substantially the same as a location of a golfer wearing the wearable device 1001. Because the golfer hits the golf ball in a state of being close to the golf ball, there may be no problem even when the location of the golfer (first location P1) is assumed to be the golf ball location P. If the mobile device 1010 is a golfer's smartphone and the golfer has his or her smartphone while playing golf, the second location P2 becomes the golfer's location. In this case, since the golfer hits the golf ball in a state of being close to the golf ball, there is no problem even when the second location P2 is assumed to be the golf ball location P. If the mobile device 1010 is spaced apart from the wearable device 1001 to some extent (for example, when the mobile device 1010 is a golfer's smartphone and the smartphone is put into a cart of a golf field), the second location P2 of the mobile device 1010 can be first ascertained through a GPS satellite signal, the first location P1 can be then ascertained from the second location P2 by tracking the location of the wearable device 1001 in the mobile device 1010 through communication between the mobile device 1010 and the wearable device 1001, and the ascertained first location P1 can be considered as the golf ball location P.

Referring to FIG. 18, information data on a golf course where a golfer is currently playing golf is stored in the storage 1012. In the third step S23, the location determiner 1011 of the mobile device 1010 extracts golf course data stored in the storage 1012 and applies a motion location (first location P1 or second location P2) where the golfer's swing is made to the extracted golf course data. The golf course data may include golf course map data representing the map of the golf course where the golfer is currently playing golf, and coordinates may be set for each location on the map. When the motion location (first location P1 or second location P2) is coupled to the golf course map on which the coordinates have been set as described above, coordinates (X, Y) indicating the golf ball location P can be ascertained.

When the location information P (X, Y) of the golf ball is ascertained through a practice swing or the like before the golf ball is hit, a distance D between the golf ball and the hole cup can be ascertained by using location information P0(X0, Y0) of the hole cup on the golf course. In addition, the ascertained distance D is displayed on the screen of the mobile device 1010 so that the distance D can be provided to the golfer. Alternatively, when the location information P (X, Y) of the golf ball indicates the location where the golfer's golf ball was hit as shown in FIG. 17, by collecting all the locations where the golf ball was hit in a specific golf course, a hitting path representing a path of locations of the golf ball during every hitting from a tee box to a hole cup can be ascertained and thus the golfer's score on the golf course can be ascertained.

Figure 19:
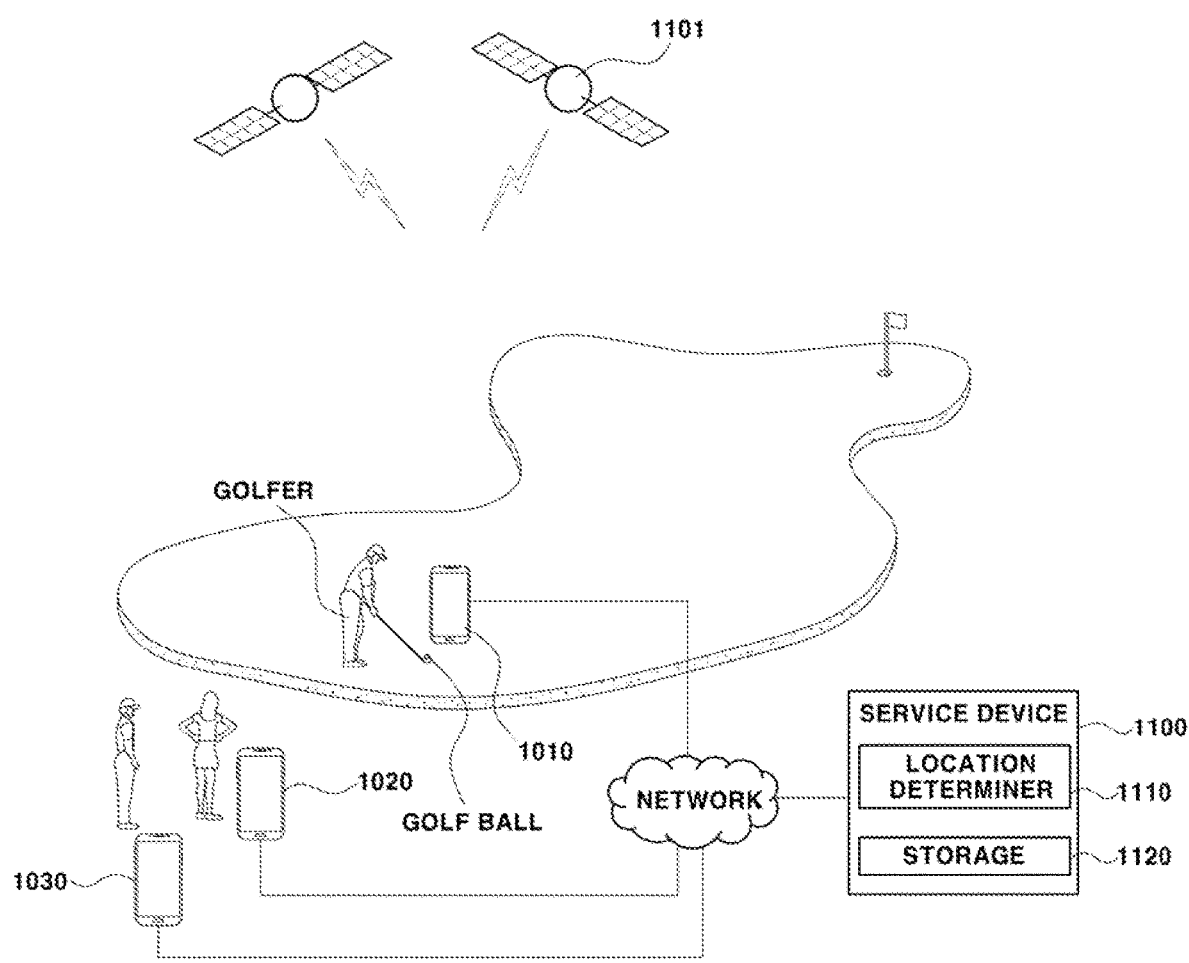
FIG. 19 is a view showing a schematic structure of a golf ball location ascertaining system according to another embodiment of the present invention.
Figure 20:
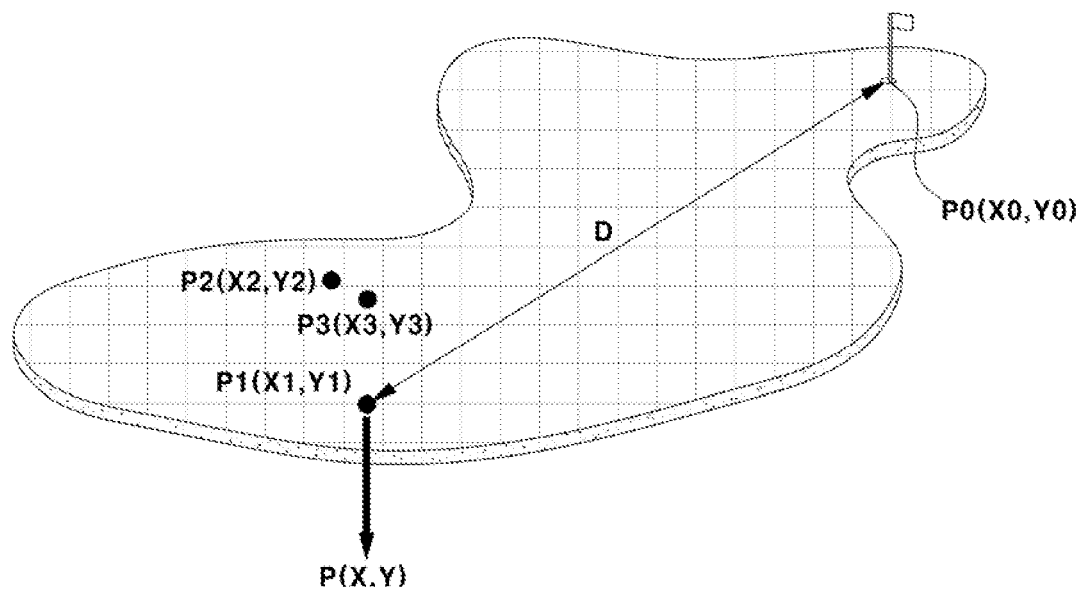
FIG. 20 is a view for explaining an operation principle when the golf ball location ascertaining system of FIG. 19 ascertains the location of a golf ball.

According to the present embodiment, when a golfer takes a specific motion and the location of a golf ball is ascertained by tracking the location of the specific motion, a significant effect can be produced by selecting a 'swing motion' as the specific motion and using a 'wristband' type wearable device to detect the swing motion. If a 'swing motion' is selected as a motion to start tracking the location of the golf ball, because the 'swing motion' is made in the vicinity of the location where the golf ball is placed, there is no problem even though the location of the swing motion is regarded as the location of the golf ball. In addition, if a motion other than a swing motion is selected as the motion for tracking the location of the golf ball, a golfer needs to take the motion separately during golf play. However, if a swing motion is selected as the motion for tracking the location of the golf ball as in the present embodiment, because the swing motion is an unconditionally necessary motion in golf play, a golfer does not need to take another separate motion in order to start tracking the location of the golf ball. Moreover, when a 'wristband' is used as a sensor for sensing the 'swing motion', the wristband can accurately catch a golfer's swing motion, because the arm of the golfer moves whenever the golfer takes a swing motion and the arm movement is transmitted naturally to the wristband worn on the wrist. Furthermore, because the wristband is worn on the wrist, the wristband does not significantly interfere with the golfer's golf play. Like this, by selecting a 'swing motion' as the motion to start tracking the location of the golf ball and using a 'wristband' type as a device that senses the 'swing motion', two components, namely, the swing motion and the wristband, are combined with each other to thereby produce a significant effect. Instead of using a separate wristband, the golfer's smartphone may be used to double the parts of the wearable device 1001 and the mobile device 1010. In other words, if the golfer attaches a smartphone to an armband while wearing the armband on his or her arm, because most smartphones have a vibration detection function, the smartphone can sense a swing motion. The location where the swing motion is made can be ascertained using a location tracking function of the smartphone, and, by applying the location where the swing motion is made to the golf course data, the location of the golf ball and various pieces of play information such as a distance between a golf ball and a hole cup) can be ascertained and provided to the golfer. FIG. 19 is a view showing a schematic structure of a golf ball location ascertaining system according to another embodiment of the present invention, and FIG. 20 is a view for explaining an operation principle when the golf ball location ascertaining system of FIG. 19 ascertains the location of a golf ball.

Referring to FIG. 19, the golf ball location ascertaining system includes mobile devices 1010, 1020, and 1030 and a service device 1100. Smartphones of golfers may be used as the mobile devices 1010, 1020, and 1030. There are a plurality of golfers, and it is assumed that the plurality of golfers have their own mobile devices 1010, 1020, and 1030. For example, when there are three golfers and they are referred to as a first golfer, a second golfer and a third golfer, the mobile devices 1010, 1020, and 1030 include a first mobile device 1010 owned by the first golfer, a second mobile device 1020 owned by the second golfer, and a third mobile device 1030 owned by the third golfer. The service device 1100 serves to ascertain the location of a golf ball and transmit the ascertained location of the golf ball to a golfer, and includes a location determiner 1110 for ascertaining the location of the golf ball and a storage 1120 for storing golf course data, etc. necessary for ascertaining the location of the golf ball. The mobile devices 1010, 1020, and 1030 and the service device 1100 are connected through a network. The mobile devices 1010, 1020, and 1030 have a location tracking function. For example, respective locations of the mobile devices 1010, 1020, and 1030 may be ascertained using the GPS satellite 1101. Because the respective locations of the mobile devices 1010, 1020, and 1030 indicate respective locations of golfers who possess them, the location of the first golfer may be ascertained through the first mobile device 1010, the location of the second golfer may be ascertained through the second mobile device 1020, and the location of the third golfer may be ascertained through the third mobile device 1030.

An operation process of ascertaining the location of the golf ball in the golf ball location ascertaining system according to the present embodiment includes a step of, by the location determiner 1110, ascertaining an motion location at which the golfer's swing motion is made (or to be made), and a step of, by the location determiner 1110, ascertaining the location of the golf ball on a golf course by applying the ascertained motion location to golf course data on a golf field of the storage 1120. Regarding the motion location, when anyone of the plurality of golfers is spaced apart from the other golfers, the current location of the golfer spaced apart from the other golfers is regarded as the motion location. For example, as shown in FIG. 20, when locations P2 and P3 of the second and third golfers are adjacent to each other and a location P1 of the first golfer is away from the locations P2 and P3 of the second and third golfers, this may mean that the first golfer is separated from the second and third golfers in order to hit his or her golf ball. Therefore, when the first golfer is located alone away from other golfers for a certain amount of time (time required for a practice swing and/or an actual swing for hitting a golf ball), under the assumption that a swing motion was made by the first golfer at that location, location information P1(X1, Y1) of the first golfer among the location information P1(X1, Y1) of the first golfer, location information P2(X2, Y2) of the second golfer, and location information P3(X3, Y3) of the third golfer may be considered to be location information P (X, Y) of the golf ball where the swing of the golf ball is made (or to be made) by the first golfer. Based on this, play information such as the distance D between the golf ball and the hole cup may be ascertained. In addition, location information of the golf ball every time a golf ball is hit may be obtained to thereby ascertain a hitting path and a score by the golf play of the golfer on a corresponding golf course. In short, when one golfer among the plurality of golfers is spaced apart from the other golfers positioned adjacent to each other for a predetermined time, it can be considered that a swing motion has been made at the location of the golfer who is away alone. However, there may other positional relationships between a plurality of golfers from which it can be considered that a swing motion has been made. AI technology may be applied to determine whether to consider that a swing motion has been made when a specific positional relationship between a plurality of golfers is formed. For example, AI technology such as machine learning is introduced into the location determiner 1110 of the service device 1100, the AI can be trained with training data in the form of $\{(x1, y1), (x2, y2), \ldots, (xn, yn)\}$ (xk (k is a natural number between 1 and n) represents a positional relationship between golfers, yk (k is a natural number between 1 and n) represents whether a golfer's swing has been made), and then the AI can determine whether to regard as a location where a swing motion has been made by checking a positional relationship between a plurality of golfers.

Figure 21:
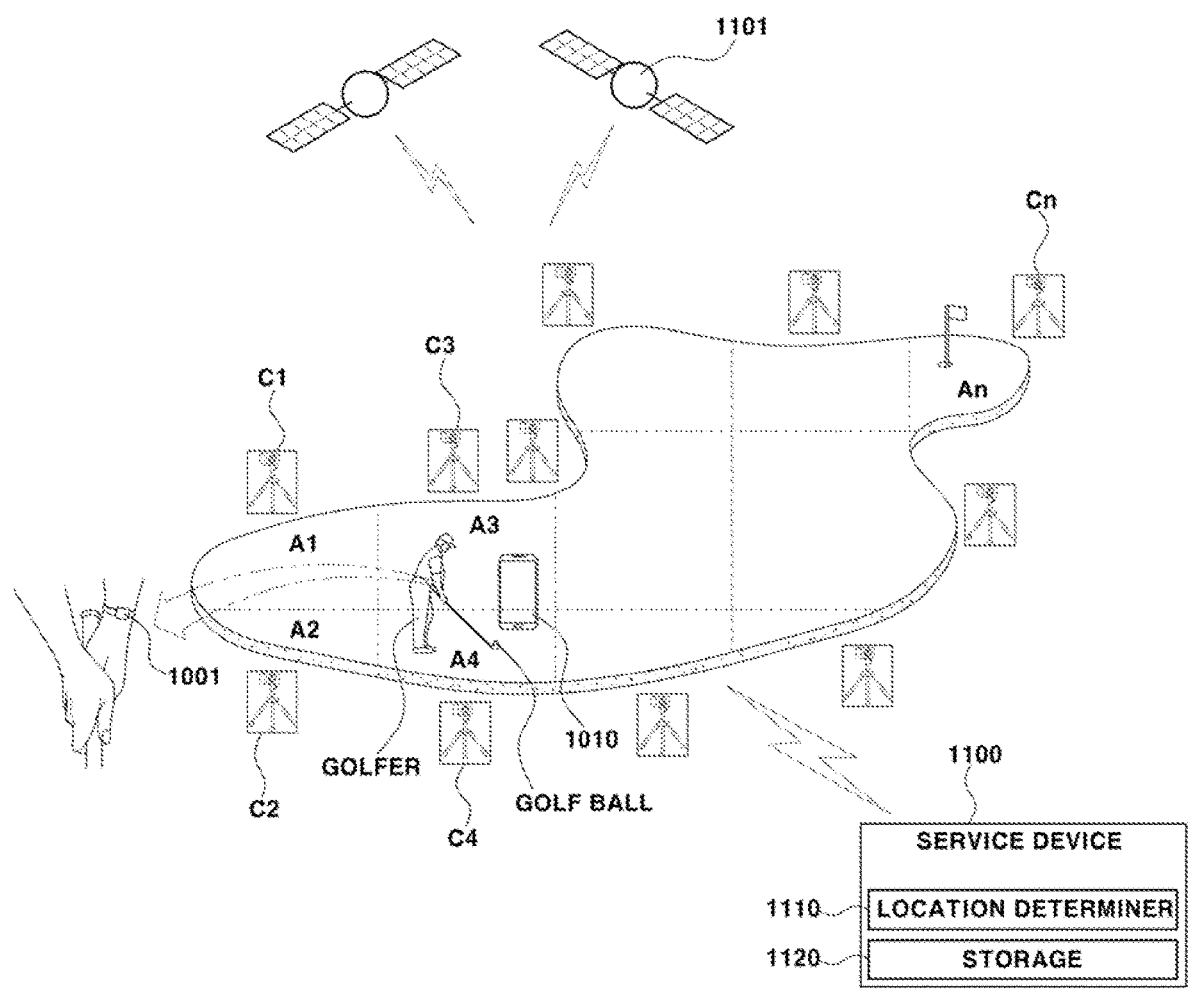
FIG. 21 is a view showing a schematic structure of a golf ball location ascertaining system according to another embodiment of the present invention.

FIG. 21 is a view showing a schematic structure of a golf ball location ascertaining system according to another embodiment of the present invention.

Referring to FIG. 21, the golf ball location ascertaining system includes a plurality of cameras C1, C2, ..., and Cn, a wearable device 1001, a mobile device 1010, and a service device 1100. The plurality of cameras C1, C2, ..., and Cn are disposed throughout the golf field, and may cover respective areas allocated thereto. For example, when the golf course of the golf field is divided into N zones and the N zones are a first area A1, a second area A2, ..., and an Nth area An (where the division areas may overlap each other or not overlap each other), N cameras C1, C2, ..., and Cn are arranged. If the N cameras C1, C2, ..., and Cn are a first camera C1, a second camera C2, ..., and an Nth camera Cn, respectively, the first camera C1 covers the first area A1, the second camera C2 covers the second area A2, ..., and the Nth camera Cn covers the Nth area An. The wearable device 1001 is worn on a golfer's body. As an example of the wearable device 1001, a wristband type device that can be worn on the golfer's wrist is used. The wristband-type wearable device 1001 may be equipped with a sensor capable of detecting a golfer's swing motion. As the mobile device 1010, a smartphone of the golfer may be used. Since the smartphone has a location tracking function through a GPS satellite 1101, the location of the mobile device 1010 can be ascertained by using the golfer's smartphone as the mobile device 1010. The service device 1100 serves to ascertain the location of a golf ball and transmit the ascertained location of the golf ball to a golfer, and includes a location determiner 1110 for ascertaining the location of the golf ball and a storage 1120 for storing golf course data, etc. necessary for ascertaining the location of the golf ball. Although not shown in the drawings, both the plurality of cameras C1, C2, ..., and Cn and the service device 1100 are provided with wireless communication means and may communicate with each other by using the wireless communication means.

The golf ball location ascertaining system according to the present embodiment includes both the configuration of the system shown in FIG. 12 and the configuration of the system shown in FIG. 15. Therefore, at least one of the golf ball location ascertaining processes in the above-described systems can be applied to the golf ball location ascertaining system according to the present embodiment. For example, two different processes (first process and second process) can be applied to the present embodiment. In the first process, a plurality of cameras C1, C2, ..., and Cn that cover a plurality of areas A1, A2, ..., and An, respectively generate photographed images for the plurality of areas, a photographed image with a golf ball is extracted from the photographed images obtained by the plurality of cameras, and then the extracted photographed image is applied to golf course data so that the location of the golf ball can be ascertained. In the second process, whether a golfer takes a swing motion is detected in the wearable device 1001 worn by the golfer, and the location where the swing motion has been made is applied to the golf course data so that the location of the golf ball can be ascertained. The first and second processes may be used in various ways. As one example, only one of the first and second processes may be carried out. As another example, both the first process and the second process may be carried out independently of each other. As another example, only one of the first and second processes may be performed and the other process may be additionally carried out only if there is a problem from the performed process. As another example, the first and second processes may be performed together in a complementary manner. Concretely, when the first and second processes are performed together in a complementary manner, steps of ascertaining the approximate position of the golf ball through the second process, generating an image photographed by a camera covering an area including the ascertained approximate location, and finally ascertaining the location of the golf ball by using the generated photographed image may be carried out. The method with these steps can make up for the point that the location of the golf ball ascertained in the second process indicates the location of the golfer and thus may be different from an exact location of the golf ball. There are merits in this method that, by proceeding with the first process after first ascertaining the location of the golf ball through the second process, the exact location of the golf ball can be ascertained and also some steps of the first process can be omitted (it is not necessary to carry out the first process for other areas of the entire golf course except for an area including a location ascertained during the second process).

Although the embodiments of the present invention have been disclosed for illustrative purposes, those skilled in the art will appreciate that the present invention may be embodied in other specific ways without changing the technical spirit or essential features thereof. Therefore, the embodiments disclosed in the present invention are not restrictive but are illustrative. The scope of the present invention is given by the claims, rather than the specification, and also contains all modifications within the meaning and range equivalent to the claims.

What is claimed is:

1. A golf ball location ascertaining method comprising:
   a step of checking whether a golfer takes a swing motion in a golf field;
   a step of ascertaining a motion location at which the swing motion is taken when it is determined that the swing motion is taken; and a step of ascertaining a location of the golf ball on a golf course by using golf course data on the golf field and the motion location, wherein there are a plurality of golfers, each of the plurality of golfers has a portable device capable of ascertaining his or her location, and whether the swing motion is made can be ascertained by checking a positional relationship between the plurality of golfers.

2. A golf ball location ascertaining method comprising:

a step of checking whether a golfer takes a swing motion in a golf field;

a step of ascertaining a motion location at which the swing motion is taken when it is determined that the swing motion is taken; and a step of ascertaining a location of the golf ball on a golf course by using golf course data on the golf field and the motion location, wherein there are a plurality of golfers, each of the plurality of golfers has a portable device capable of ascertaining his or her location, and whether the swing motion is made can be ascertained by checking a positional relationship between the plurality of golfers, and wherein when any one of the plurality of golfers is positioned to be spaced apart from the other golfers positioned adjacent to each other for a predetermined time, a current location of the spaced apart golfer is considered as the motion location at which the swing motion is taken.

3. The golf ball location ascertaining method of claim 2, wherein the step of ascertaining a location of the golf ball comprises dividing the golf course of the golf field into a plurality of areas and disposing cameras that have the same number of the plurality of divided areas and cover the divided areas respectively, generating photographed images for the divided areas using the cameras, extracting a photographed image including the golf ball among the photographed images, and ascertaining the location of the golf ball on the golf course by applying the extracted photographed image to golf course data on the area covered by the camera that is used to generate the extracted photographed image.

4. The golf ball location ascertaining method of claim 1, wherein the step of ascertaining a location of the golf ball comprises dividing the golf course of the golf field into a plurality of areas and disposing cameras that have the same number of the plurality of divided areas and cover the divided areas respectively, generating photographed images for the divided areas using the cameras, extracting a photographed image including the golf ball among the photographed images, and ascertaining the location of the golf ball on the golf course by applying the extracted photographed image to golf course data on the area covered by the camera that is used to generate the extracted photographed image.

5. A golf ball location ascertaining method comprising:

a step of checking whether a golfer takes a swing motion in a golf field;

a step of ascertaining a motion location at which the swing motion is taken when it is determined that the swing motion is taken; and a step of ascertaining a location of the golf ball on a golf course by using golf course data on the golf field and the motion location, wherein there are a plurality of golfers, each of the plurality of golfers has a portable device capable of ascertaining his or her location, and whether the swing motion is made can be ascertained by checking a relative positional relationship between the plurality of golfers.

6. The golf ball location ascertaining method of claim 5, wherein the step of ascertaining a location of the golf ball comprises dividing the golf course of the golf field into a plurality of areas and disposing cameras that have the same number of the plurality of divided areas and cover the divided areas respectively, generating photographed images for the divided areas using the cameras, extracting a photographed image including the golf ball among the photographed images, and ascertaining the location of the golf ball on the golf course by applying the extracted photographed image to golf course data on the area covered by the camera that is used to generate the extracted photographed image.

* * * * *